US012685754B2

(12) United States Patent
Chun

(10) Patent No.: US 12,685,754 B2
(45) Date of Patent: Jul. 21, 2026

(54) METHOD OF FIXATING AND STABILIZING NITRIC OXIDE METABOLITES THROUGH FERMENTATION OF NITROGEN-CONTAINING NATURAL SUBSTANCE

(71) Applicant: Hyun-Soo Chun, Seoul (KR)

(72) Inventor: Hyun-Soo Chun, Seoul (KR)

( * ) Notice: Subject to any disclaimer, the term of this patent is extended or adjusted under 35 U.S.C. 154(b) by 753 days.

(21) Appl. No.: 17/772,658

(22) PCT Filed: Oct. 29, 2020

(86) PCT No.: PCT/KR2020/014881
§ 371 (c)(1),
(2) Date: Apr. 28, 2022

(87) PCT Pub. No.: WO2021/086036
PCT Pub. Date: May 6, 2021

(65) Prior Publication Data
US 2022/0401501 A1 Dec. 22, 2022

(30) Foreign Application Priority Data

Oct. 29, 2019 (KR) ........................ 10-2019-0135814

(51) Int. Cl.
| | |
|---|---|
| *A61K 35/747* | (2015.01) |
| *A23L 33/10* | (2016.01) |
| *A61K 35/741* | (2015.01) |
| *A61K 35/742* | (2015.01) |
| *A61K 35/744* | (2015.01) |
| *A61K 35/745* | (2015.01) |
| *A61P 3/10* | (2006.01) |
| *A61P 9/12* | (2006.01) |
| *A61P 17/02* | (2006.01) |
| *C12N 1/205* | (2026.01) |
| *C12P 13/00* | (2006.01) |
| *C12R 1/125* | (2006.01) |

(52) U.S. Cl.
CPC ............ *A61K 35/747* (2013.01); *A23L 33/10* (2016.08); *A61K 35/741* (2013.01); *A61K 35/742* (2013.01); *A61K 35/744* (2013.01); *A61K 35/745* (2013.01); *A61P 3/10* (2018.01); *A61P 9/12* (2018.01); *A61P 17/02* (2018.01); *C12N 1/205* (2021.05); *C12P 13/008* (2013.01); *A23V 2002/00* (2013.01); *A23V 2400/123* (2023.08); *A23V 2400/145* (2023.08); *A23V 2400/147* (2023.08); *A23V 2400/157* (2023.08); *A23V 2400/175*

(2023.08); *A23V 2400/517* (2023.08); *A23V 2400/529* (2023.08); *A23V 2400/533* (2023.08); *C12R 2001/125* (2021.05)

(58) Field of Classification Search
CPC .. A61K 35/741; A61K 35/742; A61K 35/744; A61K 35/745
See application file for complete search history.

(56) References Cited

U.S. PATENT DOCUMENTS

| | | | | |
|---|---|---|---|---|
| 2011/0014672 A1* | 1/2011 | Chotani | ................ | C12P 5/007 435/243 |
| 2017/0020178 A1* | 1/2017 | Rubin | .................... | A23L 2/382 |

FOREIGN PATENT DOCUMENTS

| | | | |
|---|---|---|---|
| KR | 10-2008-0026356 A | | 3/2008 |
| KR | 10-1086270 B1 | | 11/2011 |
| KR | 10-2015-0121970 A | | 10/2015 |
| KR | 10-1686179 B1 | | 12/2016 |
| KR | 10-2018-0004431 A | | 1/2018 |
| KR | 20180004431 A | * | 1/2018 |
| KR | 10-2019-0084592 A | | 7/2019 |
| KR | 10-2129038 B1 | | 7/2020 |
| WO | WO 2010/034118 A1 | | 4/2010 |

OTHER PUBLICATIONS

Michiko M. Nakano, F. Marion Hulett, Adaptation of Bacillus subtilis to oxygen limitation, FEMS Microbiology Letters, vol. 157, Issue 1, Dec. 1997, pp. 1-7, https://doi.org/10.1111/j.1574-6968. 1997.tb12744.x (Year: 1997).*
International Search Report for PCT/KR2020/014881 mailed on Feb. 2, 2021.

* cited by examiner

*Primary Examiner* — Ruth A Davis
(74) *Attorney, Agent, or Firm* — The PL Law Group, PLLC

(57) ABSTRACT

A method of fixating and stabilizing nitric oxide metabolites within fermented natural substance according to an embodiment of the present disclosure includes adding a fermentative strain to nitrogen-containing natural substance and carrying out fermentation. The fermentation efficiency is maximized by optimizing the fermentation conditions so that the productivity of nitric oxide metabolites is significantly improved. Thus, eating a fermented natural substance in which nitric oxide metabolites are fixated and stabilized by the method of the present invention would be helpful for maintaining the homeostasis of human body, in which nitric oxide synthase is either absent or insufficient, based on vasodilation and activation of a neurotransmitter and immune function as medical efficacy of nitric oxide.

12 Claims, 15 Drawing Sheets

FIG. 1
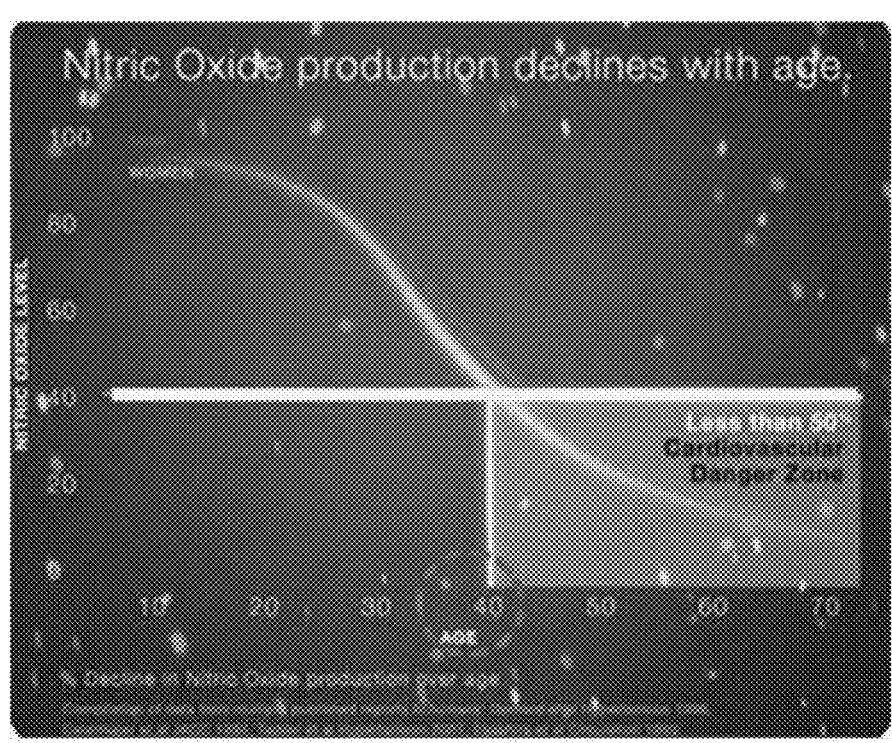
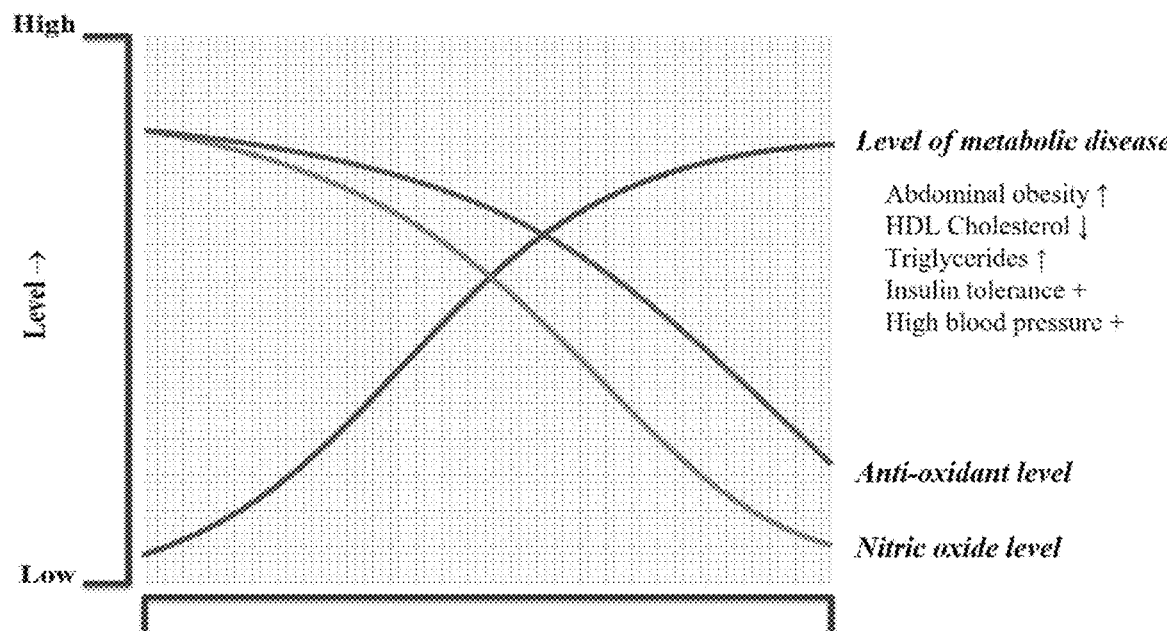
*Level of metabolic disease*
Abdominal obesity ↑
HDL Cholesterol ↓
Triglycerides ↑
Insulin tolerance +
High blood pressure +
*Anti-oxidant level*
*Nitric oxide level*

FIG. 4
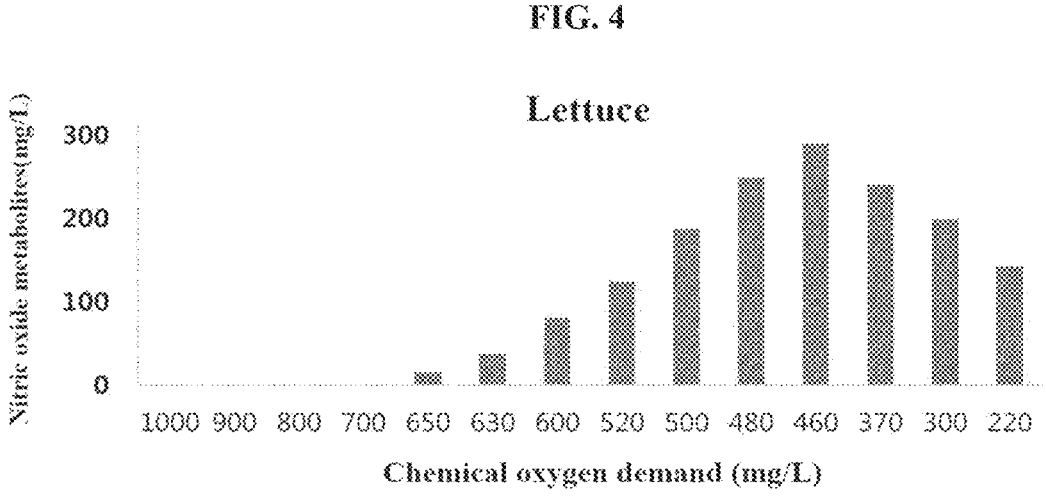
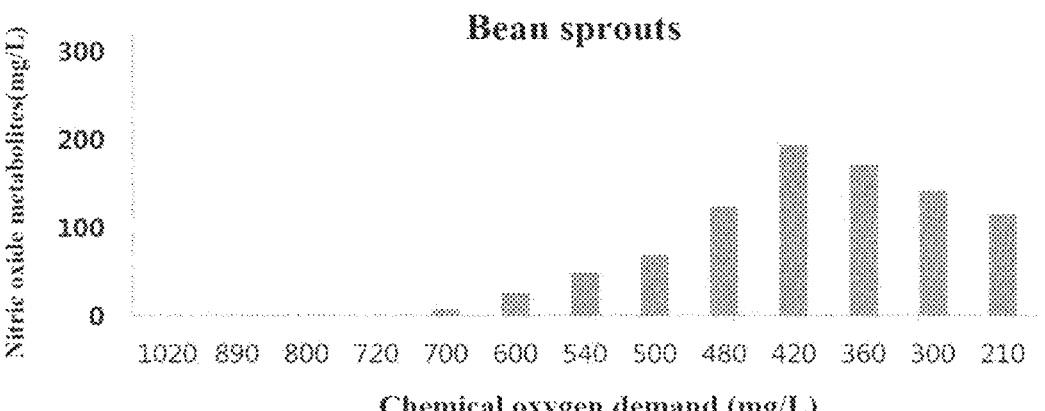
Production amount of nitric oxide metabolites depending on chemical oxygen demand at fermentation end point
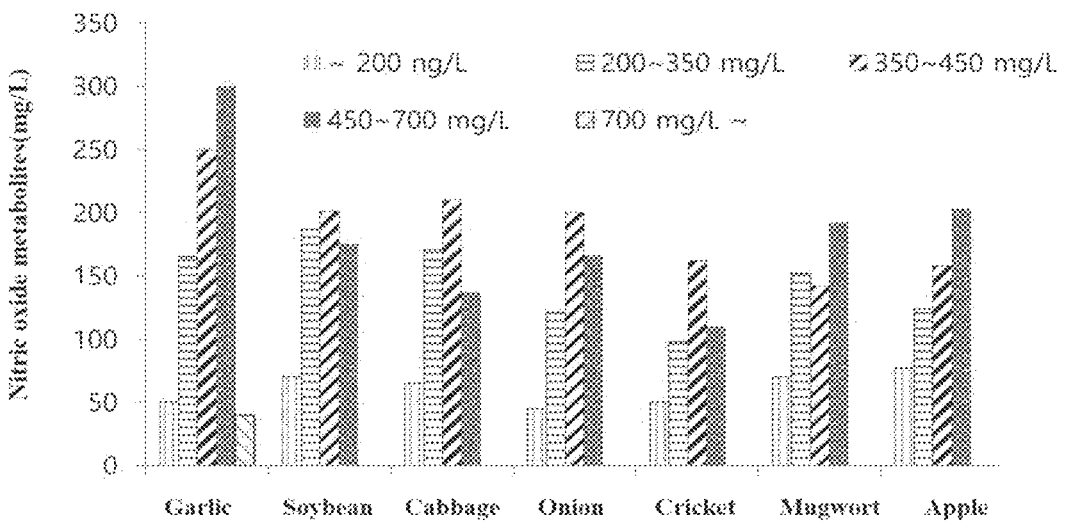

Medical Sensor-Biomaterial Research Institute

Document No.: 2019-04                          Title: Issuance of test result
Test Date: Sep. 24, 2019                        Tester: Heesoo Kim
To be received by: HTO Life
                   772-43 Bongdong-Ro, Bongdong-Up, Wanju-Gun, Chollabuk-Do

Test Result Report

■ Sample name: 1) Garlic 2) Cabbage 3) Onion 4) Bean sprouts 5) Lettuce 6) Soybean
          7) Sodium nitrite (NaNO₂) 8)Cricket ■ Test item: Amount of nitric oxide released from sample under artificial gastric juice
          and artificial intestine conditions ■ Test condition
     * Artificial gastric juice: 0.05 M HCl(75mM NaCl, 13mM KCl)
                                 0.1 M PBS(0.1M Ascorbic acid, 50 mM NaCl)
     * Test temperature: 37°C
     * Device used: Nitric Oxide Analyzer (Sievers 280i)

■ Test method:
     * Each test sample is injected to 100 ml of artificial gastric juice and 100ml
       of artificial intestinal juice, respectively, and amount of the generated nitric
       oxide is measured based on chemiluminescence ■ Test result:

| Sample name | Nitrite concentration | Theoretical value of nitric oxide | Acidic condition | | Reducing condition | | Nitrite concentration after acidic/reducing condition | |
|---|---|---|---|---|---|---|---|---|
| | mg/L | umol/ml | umol/ml | mg/L | umol/ml | mg/L | umol/ml | mg/L |
| Garlic | 265 | 8.83 | 7.59 | 227.7 | 23.43 | 702.9 | 0 | 0 |
| Cabbage | 170 | 5.67 | 2.16 | 64.8 | 5.4 | 162 | 0 | 0 |
| Onion | 205 | 6.33 | 6.5 | 195 | 9.57 | 287.1 | 0 | 0 |
| Bean sprouts | 160 | 5.33 | 5.17 | 155.1 | 11.71 | 351.3 | 0 | 0 |
| Lettuce | 280 | 9.33 | 8.7 | 261 | 15 | 450 | 0 | 0 |
| Soybean | 210 | 7.0 | 6.82 | 204.6 | 13.7 | 411 | 0 | 0 |
| Sodium nitrite | 435 | 14.50 | 4.35 | 130.7 | 16.28 | 488.4 | 0.167 | 5 |
| Cricket | 179 | 5.96 | 2.08 | 62.5 | 5.2 | 156.2 | 0 | 0 |

* Above results are the results obtained from test samples supplied by the Requester,
and the sample names were also given by the Requester. The current test result report
cannot be used for any commercial purposes including advertisement, propaganda, and
the like other than the purpose of requesting test.

September 27, 2019

Professor Jaebo Shin, Kwangwoon University
Head of Medical Sensor · Biomaterial Research Institute (01897) Room 301 Okui-gwan, Kwangwoon University
Kwangwoon-Ro 20, Nowon-Gu, Seoul, South Korea
Phone) 02-940-5246

FIG. 7

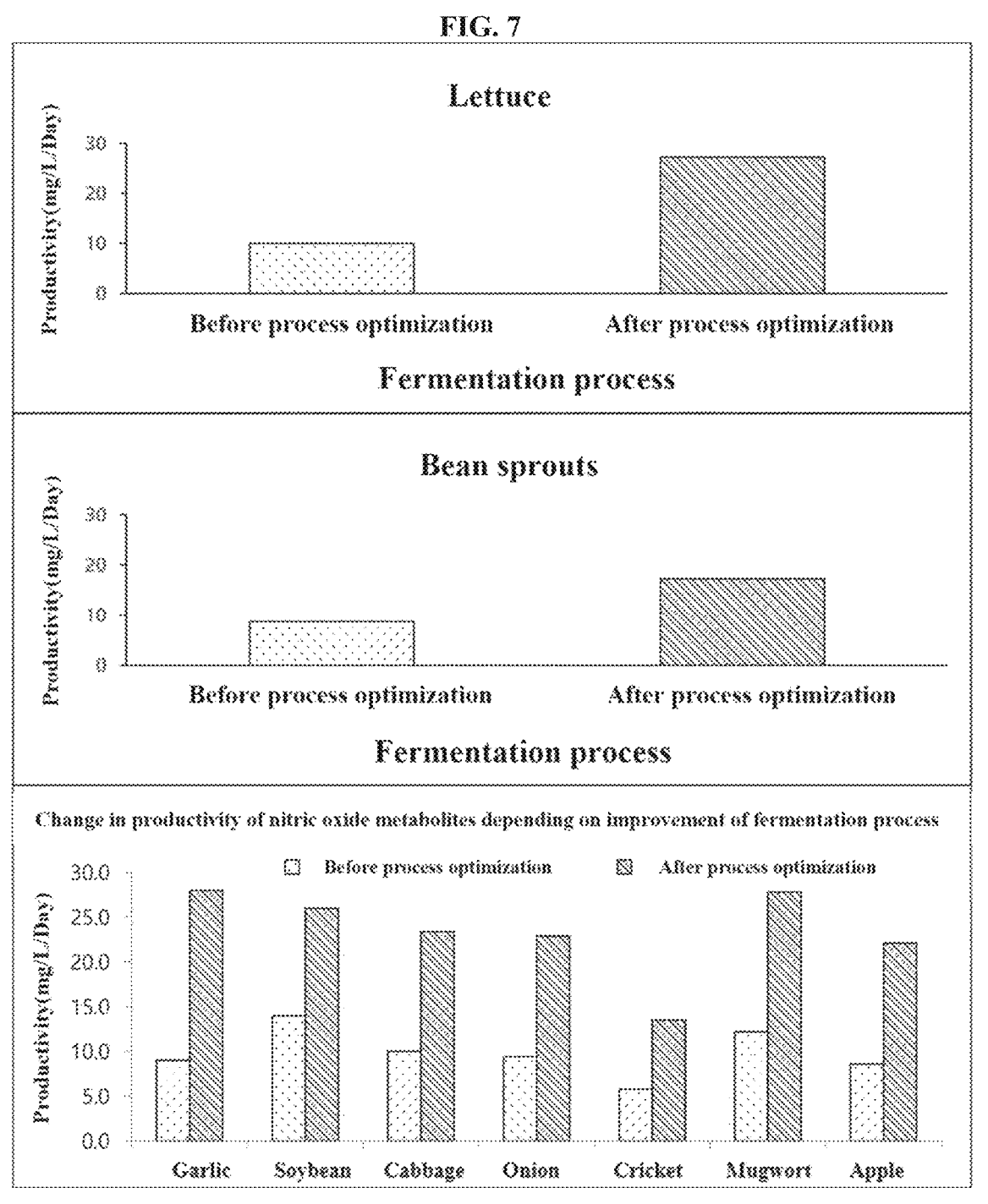

Lettuce

Bean sprouts

Change in productivity of nitric oxide metabolites depending on improvement of fermentation process FIG. 12
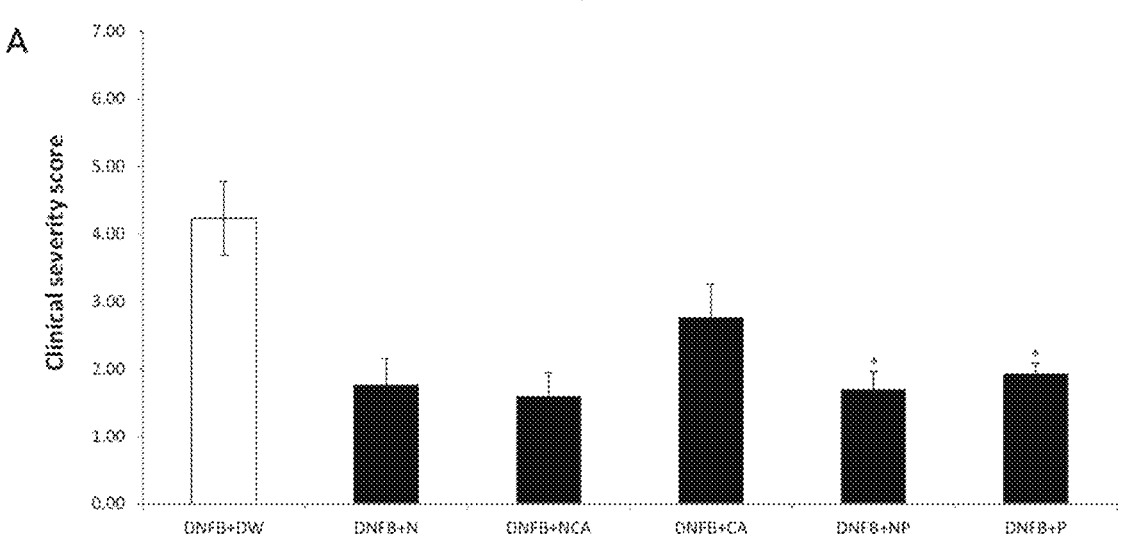
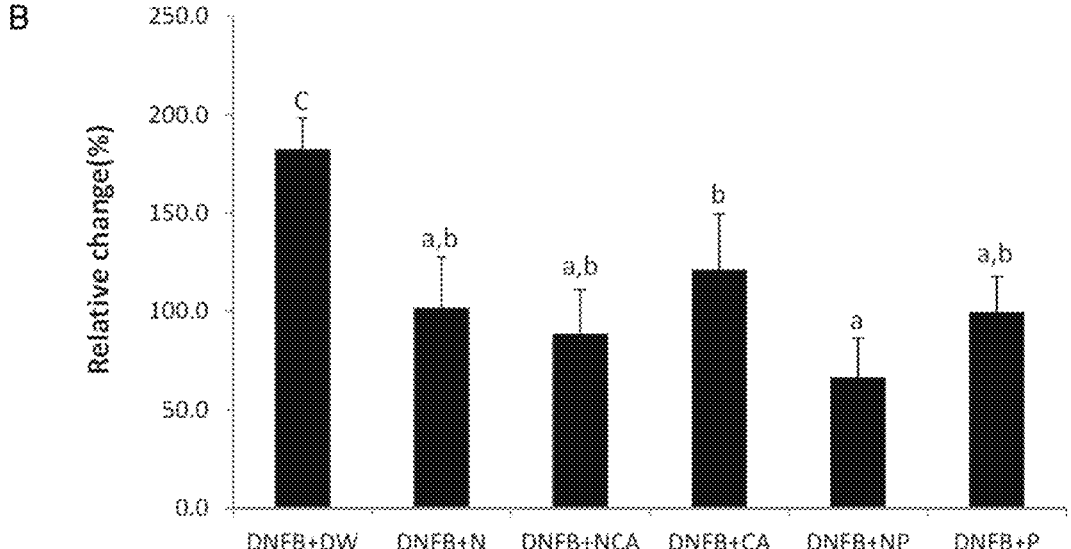
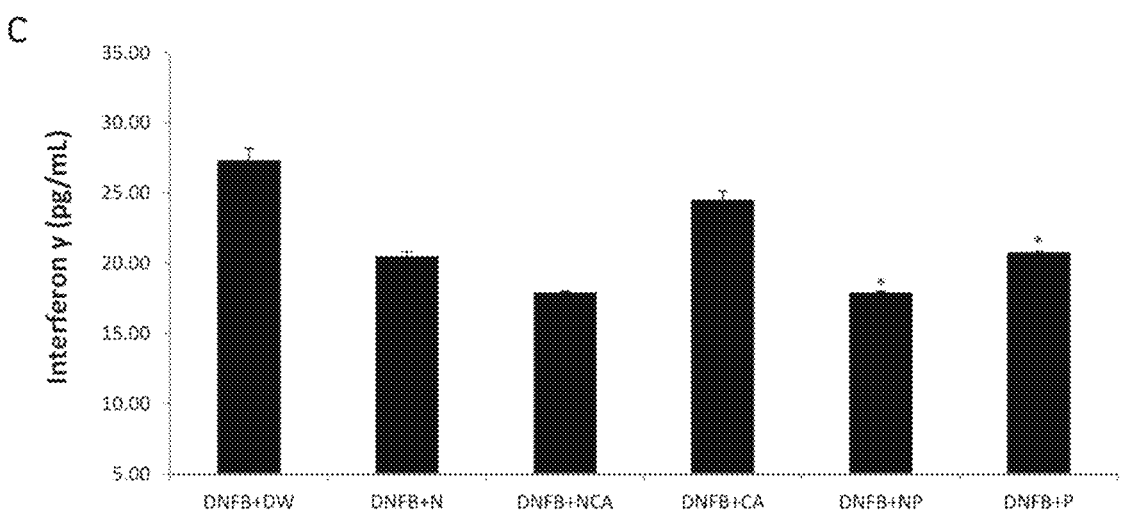

METHOD OF FIXATING AND STABILIZING NITRIC OXIDE METABOLITES THROUGH FERMENTATION OF NITROGEN-CONTAINING NATURAL SUBSTANCE

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2020/014881, filed Oct. 29, 2020, which claims priority to the benefit of Korean Patent Application No. 10-2019-0135814 filed in the Korean Intellectual Property Office on Oct. 29, 2019, the entire contents of which are incorporated herein by reference.

BACKGROUND

1. Technical Field

The present invention relates to a method of fixating and stabilizing nitric oxide metabolites through fermentation of nitrogen-containing natural substance. More specifically, the present invention relates to a method of fixating nitric oxide metabolites by producing the metabolites through fermentation of a nitrogen-containing natural substance at optimized fermentation condition and stabilizing the nitric oxide metabolites produced by fermentation.

2. Background Art

Nitric oxide (NO) is a gas molecule having very short half-life, i.e., no longer than several seconds, and it plays a very important role in maintaining homeostasis in the human body as it is involved in blood vessel expansion and immune activity, and functioning as a neurotransmitter, or the like. As illustrated in FIG. 1, until the age of 20 or so, nitric oxide is naturally produced 100% in human body. However, the production amount is down by 50% by the age of 40 or so, and it is hardly produced over the age of 70. As such, homeostasis of the human body, which is the role played by nitric oxide, cannot be maintained with aging. The homeostasis disruption is caused by the characteristics of nitric oxide produced in human body, i.e., in a cell, nitric oxide is produced from arginine by nitric oxide synthase (NOS) but the amount of nitric oxide synthase varies greatly depending on the age of human body.

There are three major types of nitric oxide synthase, i.e., inducible NOS (iNOS; Type 2 NOS), endothelial NOS (eNOS; Type 3 NOS), which is an NOS constantly expressed (i.e., constitutive NOS), and neuronal NOS (nNOS; Type 1 NOS). The problem lies in that the amount of those nitric oxide synthases diminishes with aging, and, since nitric oxide synthases themselves diminish, it is difficult to produce nitric oxide even if precursors of nitric oxide are administered from outside. In spite of the problem, a method of producing nitric oxide synthase is currently not available, and thus studies for having higher production of nitric oxide in human body are now made in the direction that either nitric oxide synthase is activated or precursors of nitric oxide involved in nitric oxide production are administered.

In Korean Patent Registration No. 1686179, cricket with enhanced effect of preventing high blood pressure and diabetes and enhanced health tonic effect and a food composition containing the cricket, which has an effect of preventing high blood pressure and diabetes and enhanced health tonic effect, by comprising an extract obtained from cricket with enhanced amount of arginine and nitric oxide are disclosed. However, since it is required to contain arginine as an effective component, it appears that production of nitric oxide is still dependent on nitric oxide synthase.

Moreover, in Japanese Laid-Open Patent Application No. 2012-503606, amino ester compounds having nitro group (i.e., $-NO_2$), nitroso group (i.e., NO), and/or heterocyclic nitric oxide-releasing group for use as a vasodilating pharmaceutical agent, and a pharmaceutical composition containing the amino ester compounds are disclosed. However, there is a limitation that the synthetic pharmaceutical preparation has toxicity and side effects.

As discussed in the above, it is now known from previous clinical trials that therapeutic methods based on administration of nitric oxide precursors like L-arginine and nitrate ($NO_3^-$) obviously have a limitation. That is because, as most people with low nitric oxide level suffer from dysfunctional endothelial cells and poor ability of converting nitric oxide, it is actually not expected to have the production of nitric oxide even when nitric oxide precursor is administered in a large amount. In addition, once turning 40 years and older, people tend to have lower nitric oxide synthase activity, and thus the contribution to produce nitric oxide from utilization of nitric oxide precursor diminishes even more. Alternatively, there is a method of treating lung disorder by directly supplying insufficient nitric oxide in gas form from outside. However, in terms of the clinical application, there is a limitation in that nitric gas is present as gas and has strong reactivity and, above all, extremely short half-life (i.e., 2 to 4 seconds).

Meanwhile, as various nitric oxide donors that can store and release nitric oxide, isosorbide mononitrate, nitroglycerine, and the like have been developed. However, they were found to exhibit the side effects like high blood pressure, headache, and resistance. In particular, when nitrate ($NO_3^-$) is administered as a nitric oxide precursor, it undergoes the pathway for conversion to nitric oxide via nitrite ($NO_2^-$). However, there is a study showing that, once remained in human body, nitrite binds to an "amine" compound in proteins to possibly produce a carcinogen named "nitrosamine." As such, in most countries including South Korea, it is required that the residual amount of nitrite ion in meat product is not higher than certain amount (i.e., 70 mg/or less in South Korea)

In particular, when a nitric oxide precursor or nitric oxide metabolites are eaten in form of food or pharmaceutical preparation, a carcinogen may be produced due to an action of gastric juice. There is also a problem that, as the effect-exhibiting period is only about 30 minutes in human stomach, the medical efficacy of nitric oxide does not last for a long period of time. Moreover, if nitric oxide reductase or nitric oxide synthase is not present in enough amount in small intestine or large intestine of a human body, appropriate conversion to nitric oxide is not obtained even when nitric oxide precursor reaches the small intestine or large intestine, and thus it is not likely to have the medical effect like controlling intestinal inflammation, immunity, or the like.

Accordingly, as one way of studying the method of effectively providing nitric oxide metabolites without any side effect instead of the nitric oxide precursor which potentially exhibits a side effect problem in human body, the inventors of the present invention studied a method of fixating and stabilizing nitric oxide metabolites via fermentation of nitrogen-containing natural substance, in which the method includes producing nitric oxide metabolites based on fermentation of a nitrogen-containing natural substance at optimized fermentation condition, maximizing the production amount of metabolites, stably fixating the produced nitric oxide metabolites in fermented substance, and, at the same time, allowing intake of the effective components that are contained in natural substance, and the inventors completed the present invention accordingly.

SUMMARY

Object of the present invention to solve the problems described above is to provide a method of fixating and stabilizing nitric oxide metabolites of a fermented natural substance by producing nitric oxide metabolites based on fermentation of a nitrogen-containing natural substance at optimized fermentation condition and stably fixating, in fermented substance, the nitric oxide metabolites that are produced by fermentation.

Another object of the present invention is to provide a fermented nitrogen-containing natural substance enabling simultaneous intake of nitric oxide metabolites produced by fermentation of a nitrogen-containing natural substance at optimized fermentation condition and effective components of the natural substance like vitamins, minerals, and phytochemicals.

Another object of the present invention is to provide a method of maximizing, compared to conventional techniques, the production amount of nitric oxide metabolites based on improvement of the fermentation process and enhancing productivity by combining the fermentation processes into a single process.

Another object of the present invention is to provide a fermented substance with nitric oxide metabolites fixated and stabilized therein by the method of fixating and stabilizing nitric oxide metabolites based on fermentation of a nitrogen-containing natural substance, and an enteric-coated tablet characterized by comprising the fermented substance.

Still another object of the present invention is to provide a pharmaceutical composition and a functional health food composition for treating or alleviating high blood pressure, diabetes, atopic dermatitis, or wound characterized in that the composition comprises a fermented substance with nitric oxide metabolites fixated and stabilized therein by the method of fixating and stabilizing nitric oxide metabolites based on fermentation of a nitrogen-containing natural substance.

To solve the problems that are described in the above, the present invention provides a method of fixating and stabilizing nitric oxide metabolites within fermented natural substance comprising adding a fermentative strain to nitrogen-containing natural substance and carrying out fermentation.

The present invention further provides a method of producing a fermented natural substance having nitric oxide metabolites fixated and stabilized therein comprising adding a fermentative strain to nitrogen-containing natural substance and carrying out fermentation, and also a fermented natural substance having nitric oxide metabolites fixated and stabilized therein produced by the aforementioned production method.

The present invention further provides an enteric-coated tablet comprising the fermented natural substance having nitric oxide metabolites fixated and stabilized therein.

The present invention still further provides a pharmaceutical composition and a functional health food composition comprising the fermented natural substance or enteric-coated tablet as an effective component.

According to the method of the present invention for fixating and stabilizing nitric oxide metabolites based on fermentation of a nitrogen-containing natural substance, the nitrogen-containing natural substance is fermented at optimized fermentation conditions to maximize the production amount of nitric oxide metabolites, and also, by combining the fermentation processes of conventional techniques into a single process, the processing time is dramatically shortened. Moreover, by stably fixating the produced nitric oxide metabolites in fermented substance, it becomes possible to have stabilized nitric oxide metabolites for long period of time with no conversion into other material. There is also the effect of enabling simultaneous intake of effective components contained in natural substance with the nitric oxide metabolites. Moreover, since the produced nitric oxide metabolites convert to nitric oxide at acidic condition without being remained as nitrite, nitrosamine, in which nitrite and amine are bound to each other, is not formed so that there is no risk of having cancer, and therefore safe. As such, when a fermented natural substance of the present invention which has nitric oxide metabolites fixated in the material based on fermentation of a nitrogen-containing natural substance is eaten, even a human body with reduced or absent nitric oxide synthase can have vasodilation, and activation of neurotransmitter and immunity, which are the medical efficacy of nitric oxide, and thus it would be useful for maintaining homeostasis of the human body.

BRIEF DESCRIPTION OF THE DRAWINGS

FIG. 1 is a graph showing the correlation between the production of nitric oxide and human age.

FIG. 4 is a graph showing the productivity of nitric oxide metabolites depending on end point of chemical oxygen demand in the method of the present invention for fixating and stabilizing nitric oxide metabolites based on fermentation of nitrogen-containing natural substance.

FIG. 5 is a graph showing the loss rate of nitric oxide metabolites depending on end point of chemical oxygen demand in the method of the present invention for fixating and stabilizing nitric oxide metabolites based on fermentation of nitrogen-containing natural substance.

FIG. 6 is the test result report of measuring nitric oxide metabolites within fermented natural substance, which has been fermented according to the method of the present invention.

FIG. 7 is a graph for comparing the productivity of nitric oxide metabolites between the method of the present invention for fixating and stabilizing nitric oxide metabolites based on fermentation of nitrogen-containing natural substance (i.e., after process optimization) and the conventional method (i.e., before process optimization).

FIG. 12 shows the result of (A) visual examination of the ear of a mouse, (B) change in the ear thickness, and (C) interferon γ, in which the mouse has been induced to have atopic dermatitis by DNFB, in which DNFB+DW: group administered with distilled water after DNFB coating on ear, DNFB–N: group administered with 1 mM nitrite after DNFB coating on ear, DNFB+NCA: group administered with 1 mM nitrite and 1 mM citrate after DNFB coating on ear, DNFB+CA: group administered with 1 mM citrate after DNFB coating on ear, DNFB+NP: group administered with 1 mM citrate and test sample after DNFB coating on ear, and DNFB+P: group administered with test sample after DNFB coating on ear. * indicates significance of p<0.05 for DNFB+DW group.

DETAILED DESCRIPTION

Figure 2:
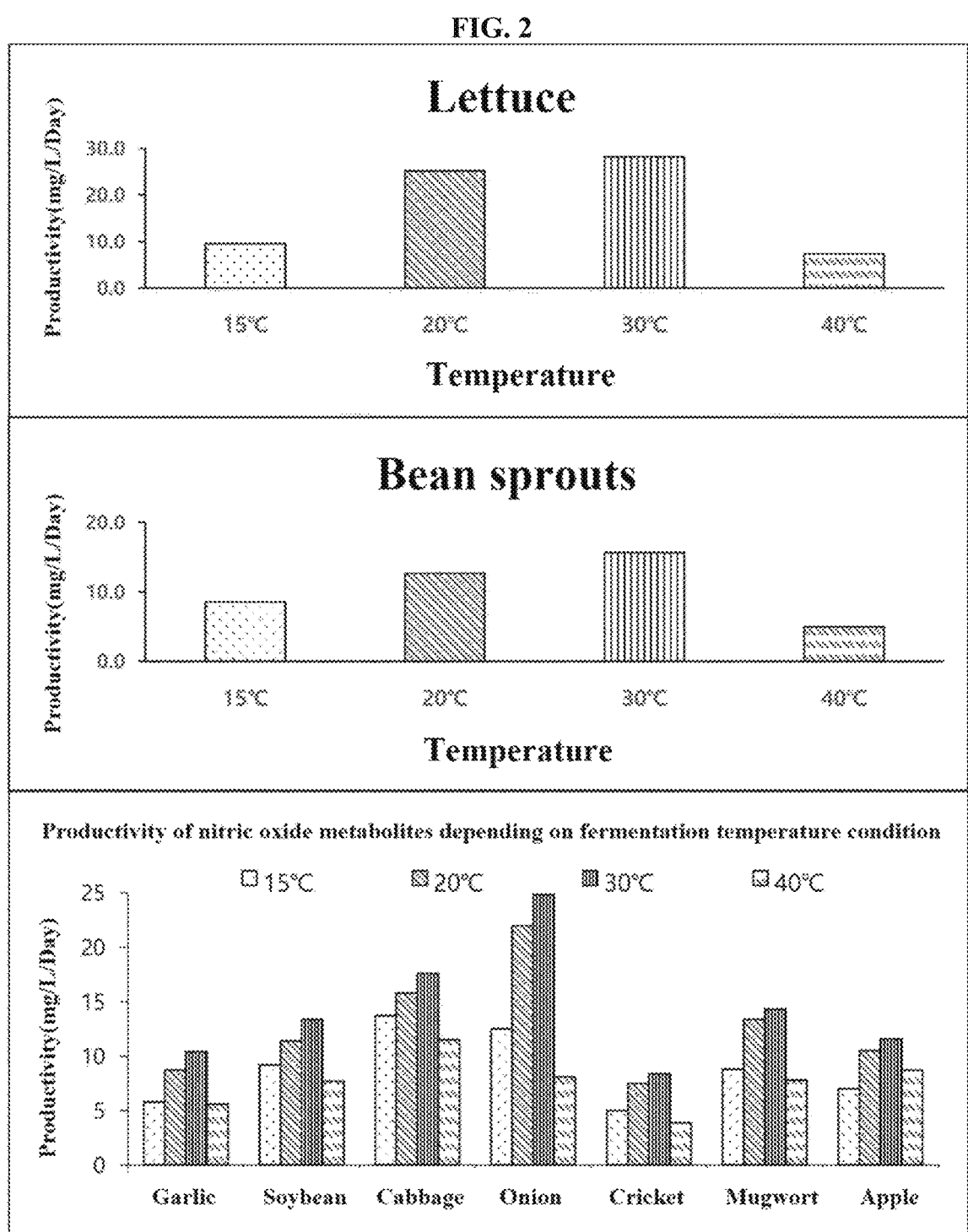
FIG. 2 is a graph showing the productivity of nitric oxide metabolites depending on fermentation temperature of the method of the present invention for fixating and stabilizing nitric oxide metabolites based on fermentation of nitrogen-containing natural substance.

To achieve the object of the present invention, provided is a method of fixating and stabilizing nitric oxide metabolites within fermented natural substance comprising adding a fermentative strain to nitrogen-containing natural substance and carrying out fermentation.

According to the method of the present invention, the aforementioned "nitric oxide metabolites" is a term which collectively refers nitric oxide (NO), nitrite ($NO_2^-$), R—NO, and R—$NO_2^-$, in which R encompasses polyphenols and fatty acids and represents a functional group to which nitric oxide or nitrite ion can bind. Under acidic or reducing conditions, conversion of nitric oxide metabolites nitric oxide is yielded. Under acidic conditions like stomach and skin, nitric oxide metabolites are oxidized by hydrogen ion ($H^+$) to generate nitric oxide while, under reducing conditions like intestine (small intestine and large intestine), nitric oxide metabolites are reduced by a reducing material like polyphenols and vitamin C to generate nitric oxide.

With regard to the method of fixating and stabilizing nitric oxide metabolites within fermented natural substance according to one embodiment of the present invention, the fermentation may be carried out by adding a fermentative strain in an amount of 0.01 to 3 parts by weight relative to 100 parts by weight of the mixture of a nitrogen-containing natural substance and water. Preferably, the fermentation may be carried out by mixing the nitrogen-containing natural substance with water at weight ratio of 1:0.5 to 1 and adding a fermentative strain in an amount of 0.01 to 3 parts by weight relative to 100 parts by weight of the mixture, but it is not limited thereto.

With regard to the method of fixating and stabilizing nitric oxide metabolites within fermented natural substance according to one embodiment of the present invention, the fermentation may be carried out at temperature of 10 to 40° C., preferably at temperature of 18 to 35° C., more preferably at temperature of 20 to 33° C., and even more preferably at temperature of 25 to 33° C., but it is not limited thereto.

Furthermore, the fermentation may be carried out at condition with dissolved oxygen concentration of 0.01 to 0.1 mg/L, and preferably 0.03 to 0.1 mg/L, but it is not limited thereto.

Furthermore, the fermentation may be carried out for 2 to 30 days, but it is not limited thereto.

Still furthermore, the fermentation may be terminated when chemical oxygen demand is 200 to 700 mg/L, but it is not limited thereto.

According to one embodiment of the present invention, it is preferable that the method is preferably carried out at fermentation temperature of 18° C. to 35° C. At the aforementioned temperature condition, the nitric oxide metabolites can be produced in a large amount and also stable fixating of a fermentation product of the produced nitric oxide metabolites can be achieved. More specifically, when fermentation is carried out by adding a fermentative strain to a nitrogen-containing natural substance, temperature inside a fermentation tank rises due to the action of a fermentative strain. In this regard, if the fermentation temperature is higher than 35° C., water vapor and gas are generated in large amount to have molds and proliferation of other harmful bacteria so that the produced nitric oxide metabolites become unstable and convert to other nitrogen compounds. Furthermore, as the fermentative strain is perished, it is not anticipated to have the production of any nitric oxide metabolites. On the other hand, if the fermentation temperature is lower than 18° C., the fermentative strain has poor proliferation activity so that, also for this case, it is not anticipated to have the production of any nitric oxide metabolites based on fermentation. Accordingly, it is preferable to have the fermentation temperature which falls within the aforementioned temperature range.

Furthermore, according to one embodiment of the present invention, it is preferable that the concentration of dissolved oxygen is maintained at 0.03 mg/L to 0.1 mg/L during fermentation. In this regard, if the concentration of dissolved oxygen is less than 0.03 mg/L, proliferation of the fermentative strain is poor so that it is not anticipated to have the production of any nitric oxide metabolites based on fermentation. In addition, because anaerobic degradation becomes dominant to yield decomposition, there would be no nutritional value, and, even if nitric oxide metabolites are produced, they cannot be stably fixated due to the decomposition gas. On the other hand, if the concentration of dissolved oxygen is more than 0.1 mg/L, the newly produced nitric oxide metabolites cannot be stably fixated and convert to other nitrogen compounds due to the oxygen present in large amount. Accordingly, it is preferable to have the concentration of dissolved oxygen which falls within the aforementioned range.

Furthermore, while the fermentation of a nitrogen-containing natural substance is carried out at the aforementioned fermentation temperature and concentration of dissolved oxygen to produce nitric oxide metabolites and the nitric oxide metabolites produced therefrom are fixated in a fermentation material, the fermentation is terminated, depending on the characteristic of a natural substance, when chemical oxygen demand reaches the level of 200 mg/L or more but not more than 700 mg/L. More specifically, when the fermentation of the fermentation process for nitrogen-containing natural substance is terminated at a condition in which chemical oxygen demand is more than 700 mg/L, the nitric oxide metabolites produced by the process convert to nitrate so that the nitric oxide metabolites cannot be fixated. On the other hand, at the chemical oxygen demand condition of less than 200 mg/L, bonds in the nitric oxide metabolites become unstable so that conversion of the nitric oxide metabolites to nitrogen ($N_2$) is caused to yield quick loss of nitric oxide metabolites. As such, it is preferable to terminate the fermentation process within the aforementioned chemical oxygen demand range.

Furthermore, with regard to the method of the present invention for fixating and stabilizing nitric oxide metabolites within fermented natural substance, the fermentative strain may be *Bacillus* sp., *Bifidobacterium* sp., *Enterococcus* sp., *Lactobacillus* sp., *Lactococcus* sp., or *Weissella* sp., and any strain selected from the group consisting of *Bacillus subtilis, B. amyloliquefaciens, B. natto, B. licheniformis, Bifidobacterium bifidum, B. infantis, B. longum, Enterococcus faecium, E. faecalis, Lactobacillus acidopilus, L. alimentarius, L. bulgaricus, L. casei, L. curvatus, L. delbrukii, L. johnsonii, L. farciminus, L. gasseri, L. helveticus, L. rhamnosus, L. reuteri, L. sakei, Lactococcus lactis*, and *Weissella cibaria* may be preferably used. Preferably, it may be *Bacillus subtilis*—Chun Hyun Su with Accession Number of KCTC12501B, but it is not limited thereto.

Furthermore, with regard to the method of the present invention for fixating and stabilizing nitric oxide metabolites within fermented natural substance, the nitrogen-containing natural substance may be, although not limited thereto, one or more selected from the group consisting of lettuce, *Sedum sarmentosum*, spinach, blueberry, dandelion, pomegranate, cabbage, garlic, *Morinda citrifolia*, onion, soybean, bean sprout, mulberry leaf, *Momordica charantia, Rubus coreanus, Houttuynia cortada*, aronia, *Humulus japonicus, Coptis chinensis*, hijiki, hooker chive, mushrooms, calamus, wild spinach (Seomcho), Chinese cabbage, kelp, salmon testis, abalone shell, shellfish shell, cricket, apple, mugwort, orange, silkworm, *Rehmannia glutinosa*, and Shipjeon-daebo-tang.

Before mixing with water and addition to a fermentation tank, the nitrogen-containing natural substance may be subjected to a grinding treatment. The grinding treatment is, although not particularly limited, preferably from ultrafine grinding to grinding to the size of 1 to 15 mm. With grinding treatment, the reaction surface is increased so that the reactivity can be maximized and yield of the nitric oxide metabolites can be also maximized.

The present invention further provides a method of producing a fermented natural substance having nitric oxide metabolites fixated and stabilized therein comprising adding a fermentative strain to nitrogen-containing natural substance and carrying out fermentation, and also a fermented natural substance having nitric oxide metabolites fixated and stabilized therein produced by the aforementioned production method.

Specifically, the method of producing a fermented natural substance having nitric oxide metabolites fixated and stabilized therein according to one embodiment of the present invention may include steps of:

(a) adding *Bacillus subtilis* strain with Accession Number of KCTC12501BP in an amount of 0.01 to 3 parts by weight relative to 100 parts by weight of a mixture in which a nitrogen-containing natural substance and water are admixed with each other at weight ratio of 1:0.5 to 1; and (b) fermenting the mixture of a nitrogen-containing natural substance and water, to which the *Bacillus subtilis* strain has been added, for 2 to 30 days at temperature of 18 to 35° C. and dissolved oxygen concentration of 0.03 to 0.1 mg/L, but it is not limited thereto.

Furthermore, the fermentation of the above step (b) may be terminated when chemical oxygen demand concentration is 200 to 700 mg/L so that the production of nitric oxide metabolites within fermented natural substance can be maximized and also stabilized.

With regard to the method of the present invention for producing a fermented natural substance having nitric oxide metabolites fixated and stabilized therein, the nitrogen-containing natural substance is as defined in the above.

Furthermore, with regard to the method of producing a fermented natural substance having nitric oxide metabolites fixated and stabilized therein according to one embodiment of the present invention, nitric oxide precursors such as nitrate or ammonia are generated as nitrogen-containing natural substance is fermented and degraded during the fermentation step, and, at the same time, the precursors are reduced by mineral components like iron, manganese, potassium, magnesium, zinc, copper, and sodium contained in the nitrogen-containing natural substance to generate nitric oxide metabolites, and the nitric oxide metabolites produced therefrom are subsequently fixated in the fermented substance. Furthermore, in addition to the nitric oxide metabolites, since materials like vitamin, mineral, and flavonoid contained in natural substance are also contained in large amount in the final fermented natural substance, there is an advantage that, by eating a fermented natural substance having nitric oxide metabolites fixated therein, useful materials of the natural substance as well as the nitric oxide metabolites can be simultaneously utilized. In addition, because a natural substance is used as a raw material, there is another advantage that the side effects and resistance in human body can be kept at minimal level.

The present invention further provides an enteric-coated tablet comprising the fermented natural substance having nitric oxide metabolites fixated and stabilized therein.

As described herein, the term "enteric-coated tablet" means a tablet coated with formulation film to prevent degradation in acidic stomach but to promote degradation in alkali intestine, and it indicates a tablet expected to prevent irritation of stomach mucosa layers, vomit, and degradation of digestive enzymes by gastric juice, and have proper functioning in intestine.

Amount of the nitric oxide in human body can be estimated as total amount of $NO_2^-$ and $NO_3^-$. Concentration of nitric oxide suitable for actual use can be estimated by blood NO concentration based on the concentration of $NO_2^-$ which can be transformed into nitric oxide. As a natural oxide metabolite, $NO_2^-$ is a hydrophilic and relatively stable ionic material. Being dissolved in blood and body fluid, it can travel to any part of the human body, but it cannot pass through an organ wall, blood vessel wall, cell membrane, or the like. When nitric oxide metabolites are orally taken to increase the low blood concentration of nitric oxide metabolites or to decrease high blood glucose level, three health-threatening problems like those described below may be caused.

First, due to the strong acidic condition of gastric juice, when $NO_2^-$ is orally taken, an excess amount of nitric oxide is absorbed by human body in a short period of time, and thus dramatic decrease in blood pressure, low blood glucose level, cyanosis, or the like may be caused. Second, due to the strong acidic condition of gastric juice, orally taken $NO_2^-$ may react with secondary amine (hereinafter, described as $R_2N$—H) to produce N-nitrosamine (hereinafter, described as $R_2N$—N═O), which is known as a carcinogenic material. Third, orally taken $NO_2^-$ is not reduced in stomach but reduced to nitric oxide in small and large intestines and then absorbed into the human body. However, the reduction level to nitric oxide varies depending on vegetable (polyphenol) diet as well as bacterial environment in intestine of an individual, and thus it is not expected to have effective absorption of a constant amount of nitric oxide.

The enteric-coated tablet according to the present invention can be a tablet developed by encapsulating a composition comprising a mixture of nitric oxide metabolites and polyphenol, which allows, after delivery to small intestine or large intestine, production of nitric oxide at constant concentration for a certain period of time without exposing the nitric oxide metabolites included in fermented natural substance to strong acidic condition of gastric juice.

Furthermore, with regard to the enteric-coated tablet of the present invention, the fermented natural substance having nitric oxide metabolites fixated and stabilized therein may preferably a material which contains $NO_2^-$ at 200 ppm or more, but it is not limited thereto.

By orally taking the enteric-coated tablet of the present invention which comprises fermented natural substance having nitric oxide metabolites fixated and stabilized therein, the nitric oxide metabolites are reduced to nitric oxide and absorbed in intestine so that clinical effects like cardiovascular control, anti-coagulation response, inflammation and immune control, activity as a neurotransmitter, or the like can be obtained.

The present invention further provides a pharmaceutical composition comprising, as an effective component, the fermented natural substance having nitric oxide metabolites fixated and stabilized therein, or the enteric-coated tablet containing the fermented natural substance.

The pharmaceutical composition of the present invention may be used for preventing or treating high blood pressure, diabetes, atopic dermatitis, or wound, but it is not limited thereto.

Furthermore, with regard to the pharmaceutical composition of the present invention, the fermented natural substance having nitric oxide metabolites fixated and stabilized therein may preferably a material which contains $NO_2^-$ at 200 ppm or more, and fermented natural substance may be used in concentrate liquid form or solidified product form, but it is not limited thereto. In addition, the concentrate liquid or solidified product may be more preferably used after coating, but it is not limited thereto.

With regard to the pharmaceutical composition of the present invention, the fermented natural substance may be preferably contained in an amount of 40 mg/g to 140 mg/g based on the total amount of the pharmaceutical composition. More preferably, it is contained in an amount of 60 mg/g to 120 mg/g, and even more preferably, it is contained in an amount of 90 mg/g to 110 mg/g.

Furthermore, the pharmaceutical composition may be used after formulated into oral formulation roam like granule, tablet, and capsule according to a common method that is suitable for the purpose of use. The composition may be administered either orally or rectally.

Examples of a suitable carrier, vehicle, and diluent which may be contained in the pharmaceutical composition include lactose, dextrose, sucrose, sorbitol, mannitol, xylitol, erythritol, maltitol, starch, acacia gum, alginate, gelatin, calcium phosphate, calcium silicate, cellulose, methyl cellulose, non-crystalline cellulose, polyvinyl pyrrolidone, water, methylhydroxy benzoate, propylhydroxy benzoate, talc, magnesium stearate, and mineral oil. Moreover, the pharmaceutical composition may additionally comprise a filler, an anti-coagulant, a lubricant, a wetting agent, a fragrance, an emulsifier, a preservative, or the like.

Moreover, when administered in a pharmaceutically effective amount to a patient with high blood pressure, diabetes, or atopic dermatitis, the pharmaceutical composition of the present invention can be used for prevention and treatment of high blood pressure, diabetes, or atopic dermatitis. In addition, as the pharmaceutical composition comprising fermented natural substance of the present invention also has an excellent skin cell regeneration effect, it can be effectively used for a treatment of wound.

The composition of the present invention may be administered as an individual therapeutic agent or in combination with other therapeutic agent. It may be administered either sequentially or simultaneously with a conventional therapeutic agent, and also can be administered just once or several times. It is important to administer, in consideration of all elements that are described above, the composition in an amount which allows obtaining the maximum effect at smallest dose without having any side effect, and the amount can be easily determined by a person who is skilled in the pertinent art.

Specifically, the pharmaceutically effective amount of the pharmaceutical composition comprising the fermented natural substance having nitric oxide metabolites fixated and stabilized therein may vary depending on age, sex, and body weight of a patient. In general, 2 mg to 4 mg, and preferably 3 mg of the composition are administered per kg of patient body weight, either every day or every other day, and it may be administered once daily, or divided doses may be administered up to 3 times per day. However, as the amount can be either increased or reduced depending on administration route, severity of disorder, sex, body weight, and age of a patient, or the like, by no means the scope of the present invention is limited by the administration amount described in the above.

The present invention still further provides a functional health food composition comprising, as an effective component, the fermented natural substance having nitric oxide metabolites fixated and stabilized therein, or the enteric-coated tablet containing the fermented natural substance.

The functional health food composition of the present invention may be used for preventing or alleviating high blood pressure, diabetes, atopic dermatitis, or wound, but it is not limited thereto.

The functional health food composition of the present invention encompasses a functional health food, a supplementary health food, and the like. Type of the composition is not particularly limited, and it encompasses a food of any type including liquid state, solid state, and other fluid state.

For example, when the functional health food composition of the present invention is a food composition like functional drink, the food composition may contain, other than the effective component, a sweetening agent, a flavoring agent, a physiologically active component, mineral, and the like.

The sweetening agent may be used in an amount for providing a food with appropriate sweetness, and it may be either a natural agent or a synthetic agent. Preferably, a natural sweetening agent is used, and examples of the natural sweetening agent include sugar sweetening agent like corn syrup in solid form, honey, sucrose, fructose, lactose, and maltose.

The flavoring agent may be used to improve taste or flavor, and either a natural agent or a synthetic agent may be used. Preferably, a natural flavoring agent is used. When a natural flavoring agent is used, object of nutritional fortification can be also achieved in addition to flavoring. Examples of the natural flavoring agent include an agent obtained from apple, lemon, orange, grape, strawberry, peach, or the like and an agent obtained from green tea leaf, Solomon's seal, bamboo leaf, cinnamon, *chrysanthemum* leaf, jasmine or the like. In addition, a flavoring agent obtained from *ginseng* (red *ginseng*), bamboo shoot, aloe vera, ginkgo or the like may be also used. The natural flavoring agent may be a concentrate in liquid state or an extract in solid state. Depending on a case, a synthetic flavoring agent may be used, and examples of the synthetic flavoring agent that can be used include ester alcohol, aldehyde, terpene, or the like.

Examples of the physiologically active material that can be used include catechins such as catechin, epicatechin, gallocatechin, or epigallocatechin, and vitamins such as retinol, ascorbic acid, tocopherol, calciferol, thiamine, or riboflavin. Examples of the mineral that can be used include calcium, magnesium, chrome, cobalt, copper, fluorides, germanium, iodine, iron, lithium, magnesium, manganese, molybdenum, phosphorus, potassium, selenium, silicon, sodium, sulfur, vanadium, and zinc.

Furthermore, the functional health food composition of the present invention may comprise, in addition to the aforementioned sweetening agent or the like, a preservative, an emulsifier, an acidulant, a thickening agent, or the like, if necessary. Those preservative, emulsifier, and the like are preferably used after being added in an extremely small amount as long as the use of their addition is attained. The extremely small amount means, in terms of numeric expression, a range of from 0.0005% by weight to about 0.5% by weight based on the total weight of the food composition. Examples of the preservative include calcium sorbate, sodium sorbate, potassium sorbate, calcium benzoate, sodium benzoate, potassium benzoate, and EDTA (ethylene diamine tetraacetic acid), and examples of the emulsifier include acacia gum, carboxymethyl cellulose, xanthan gum, and pectin. Examples of the acidulant include citric acid, malic acid, fumaric acid, adipic acid, phosphoric acid, gluconic acid, tartaric acid, ascorbic acid, acetic acid, and phosphoric acid, but it is not limited thereto. Other than the purpose of enhancing taste, those acidulants may be also added such that the food composition can have suitable acidity for the purpose of inhibiting microbial proliferation. In addition, examples of the thickening agent include a suspending agent, a precipitating agent, a gel forming agent, and a swelling agent.

Hereinbelow, the present invention is explained in greater detail in view of the Examples. However, the following Examples are given only for specific explanation of the present invention and it is evident that the scope of the present invention is not limited by them.

EXAMPLES

Example 1. Optimization of Fermentation Condition for Fermented Natural Substance Containing Nitric Oxide As a nitrogen-containing natural substance, lettuce and bean sprouts were used. After washing, each material, i.e., 300 g of lettuce or 300 g of bean sprouts, was admixed with 300 g of distilled water and then added to a grinder for grinding treatment such that the ground material has mean diameter of 4 mm. To 600 g of the ground material, 5 g of *Bacillus subtilis*—Chun Hyun Su (Accession Number KCTC12501BP) were added ($1.0 \times 10^8$ cfu/ml) and fermentation was allowed to occur.

To figure the optimum fermentation condition allowing fixating and stabilization of the nitric oxide metabolites at the highest level, production amount of nitric oxide metabolites was examined depending on various fermentation temperatures, dissolved oxygen concentrations (level), and chemical oxygen demands. For measuring the nitric oxide metabolites, amount of nitric oxide was measured under acidic condition and also reducing condition using a chemical method and calculation was made for the nitric oxide metabolites. As for the acidic condition, a condition mimicking human stomach was created using hydrochloride (HCl) solution with sodium chloride (NaCl) and potassium chloride (KCl), and then nitric oxide metabolites were released in the solution. As for the reducing condition, to mimic the condition inside human intestine, vitamin C (ascorbic acid) and sodium chloride were admixed with each other in phosphate buffer solution to create reducing condition, and then nitric oxide metabolites were released in the solution. Thereafter, by using a nitric oxide detector (Sievers Nitric Oxide Analyzer 280i), amount of the nitric oxide metabolites fixated in fermented substance was measured.

1-1. Analysis of Productivity of Nitric Oxide Metabolites Depending on Fermentation Temperature First of all, as a result of measuring the production amount of nitric oxide metabolites at different fermentation temperature (15° C., 20° C., 30° C., and 40° C.) and analyzing the productivity of nitric oxide metabolites at each temperature condition, it was shown as illustrated in FIG. 2 that lettuce and bean sprouts have the productivity of 28.2 mg/L/day and 15.7 mg/L/day, respectively, at fermentation temperature of 30° C., indicating higher productivity compared to other temperature conditions. Moreover, also in a case of producing the fermented natural substance by using garlic, soybean, cabbage, onion, cricket, mugwort, or apple, it was found that the highest productivity of nitric oxide is obtained at 30° C. compared to other temperature conditions.

Figure 3:
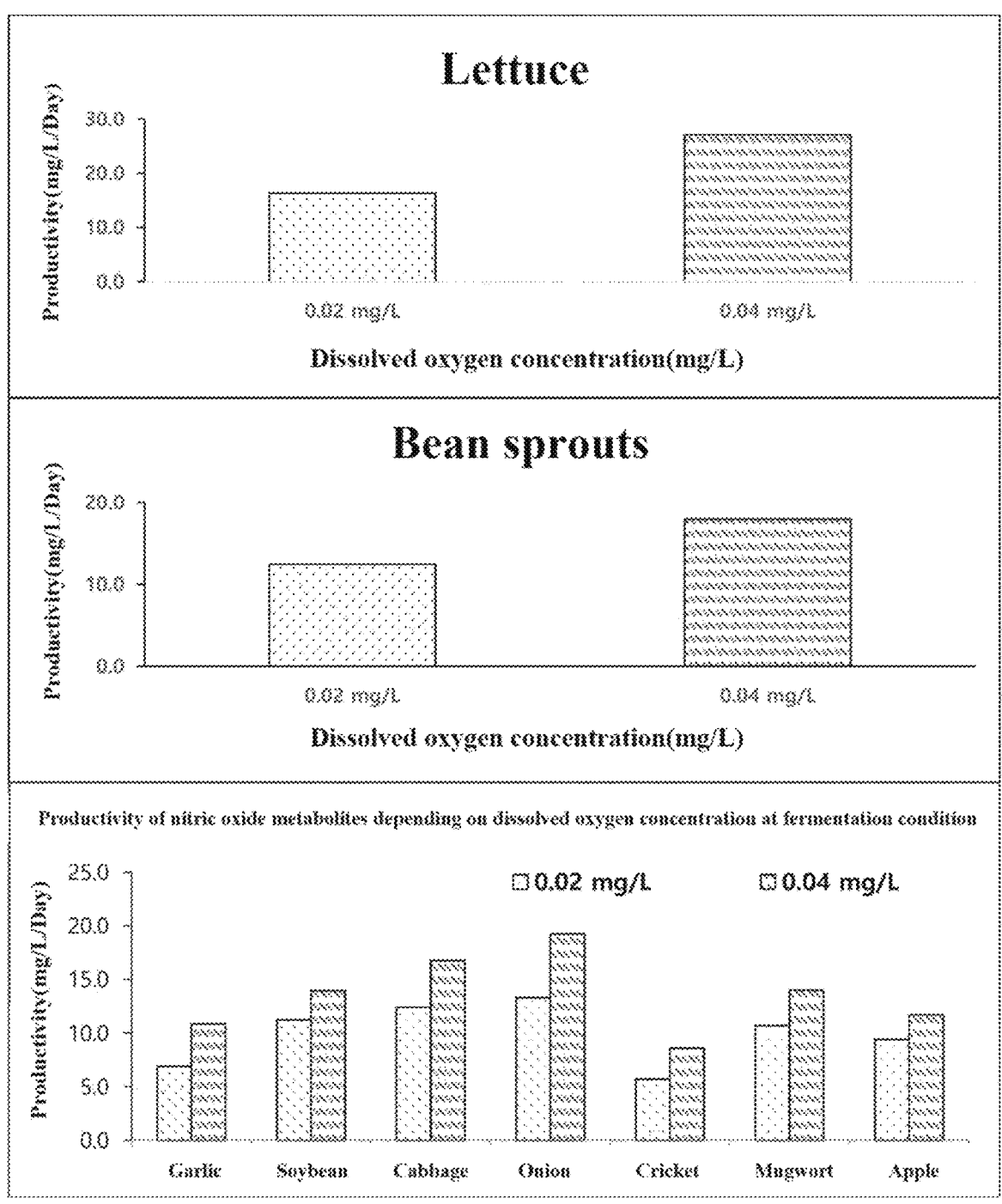
FIG. 3 is a graph showing the productivity of nitric oxide metabolites depending on concentration of dissolved oxygen in the method of the present invention for fixating and stabilizing nitric oxide metabolites based on fermentation of nitrogen-containing natural substance, in which the measurement result is obtained by examining the fermented product after fermentation for 11 days.

1-2. Analysis of Productivity of Nitric Oxide Metabolites Depending on Dissolved Oxygen Level During Fermentation Productivity of nitric oxide metabolites depending on the dissolved oxygen level during fermentation process of the fermented natural substance according to the present invention is shown in FIG. 3. As a result of carrying out the fermentation at different dissolved oxygen level, i.e., 0.02 mg/L or 0.04 mg/L, and comparing the productivity of nitric oxide metabolites between them, it was found from both the lettuce and bean sprouts that, when the fermentation was carried out at dissolved oxygen level of 0.04 mg/L, the productivity of natural oxide metabolite is higher by 1.7 times (lettuce) or 1.4 times (bean sprouts) than the condition in which the fermentation was carried out at dissolved oxygen level of 0.02 mg/L.

1-3. Analysis of Production Amount of Nitric Oxide Metabolites Depending on Chemical Oxygen Demand at Fermentation End Point Production amount of the nitric oxide metabolites depending on chemical oxygen demand at fermentation end point of natural substance was analyzed.

As illustrated in FIG. 4, it was found that, in case of fermented lettuce, the production amount of nitric oxide metabolites is 200 mg/L or higher when the chemical oxygen demand is 300 to 480 mg/L at the fermentation end point (Day 11), which is higher than the amount of other concentration ranges. Moreover, when the chemical oxygen demand is 700 mg/L or higher, production of nitric oxide metabolites was not exhibited. Similar tendency was also obtained from the fermented bean sprouts. Specifically, it was found that, when the chemical oxygen demand is 210 to 480 mg/L at the fermentation end point (Day 11), the production amount of nitric oxide metabolites is higher than the amount from other concentration ranges.

Also for garlic, soybean, cabbage, onion, cricket, mugwort, and apple, concentration of the nitric oxide metabolites fixated in fermented substance was measured for various ranges of the chemical oxygen demand at fermentation end point, i.e., less than 200 mg/L, 200 mg/L or more but less than 350 mg/L, 350 mg/L or more but less than 450 mg/L, 450 mg/L or more and 700 mg/L or less, and more than 700 mg/L. As a result, it was found that the chemical oxygen demand at end point, at which the highest production of nitric oxide metabolites is exhibited, varies depending on the type of a natural substance. Nevertheless, it was shown that, in all natural substances except garlic, production of the nitric oxide metabolites is not observed when the chemical oxygen demand is higher than 700 mg/L.

1-4. Analysis of Stability of Nitric Oxide Metabolites Depending on Chemical Oxygen Demand at Fermentation End Point In FIG. 5, analyzed result of the loss rate of nitric oxide metabolites is shown for various ranges of the chemical oxygen demand at fermentation end point, i.e., 200 mg/L or more but less than 350 mg/L, 350 mg/L or more but less than 450 mg/L, and 450 mg/L or more and 700 mg/L or less.

Specifically, after storing the fermented substance which has been obtained after completion of the fermentation process for 1 year at room temperature, nitric oxide metabolites in the fermented substance after storage was measured, and then calculation was made based on comparison with the measured amount of nitric oxide metabolites at the end point of fermentation process.

Figure 5:
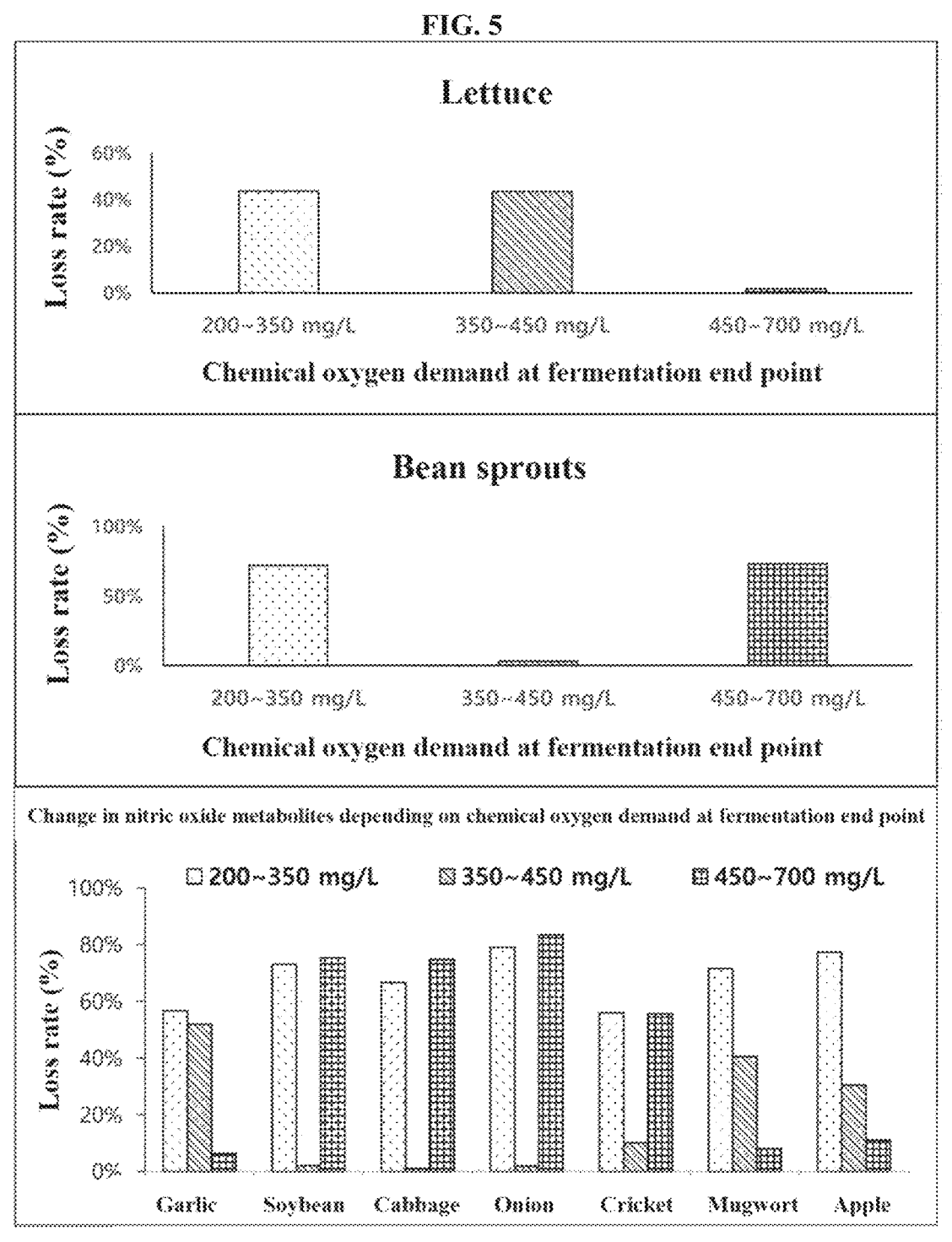

In case of lettuce, it was found that, at chemical oxygen demand of 450 mg/L or more and 700 mg/L less as the optimum end point, the loss rate of nitric oxide metabolites is significantly lower than the rate of other conditions (i.e., 200 to 350 mg/L and 350 to 450 mg/L). It was found from the bean sprouts that, at chemical oxygen demand of 350 mg/L or more but less than 450 mg/L as the optimum end point, the loss rate of nitric oxide metabolites is significantly lower than the rate of other conditions. In case of the nitrogen-containing natural substances other than lettuce and bean sprouts, it was found that the smallest loss rate is obtained at the optimum end point of chemical oxygen demand, which varies depending on the type of a natural substance as illustrated in FIG. 5. It was found that the end point of chemical oxygen demand in fermentation of a nitrogen-containing natural substance varies depending on the type of a natural substance, and, as the nitric oxide metabolites are stabilized depending on the optimum end point of chemical oxygen demand, different loss rate values are yielded. It was recognized based on the above results that, if the chemical oxygen demand is not within the range of 200 to 700 mg/L, the produced nitric oxide metabolites cannot stay in stable state and convert to other material so that the fermentation needs to be ended. In this regard, the reason behind this result is believed to be as follows, i.e., when the fermentation is terminated at chemical oxygen demand of more than 700 mg/L, the produced nitric oxide metabolites convert to nitrates to prevent stabilization of the nitric oxide metabolites, and, when chemical oxygen demand is less than 200 mg/L, the nitric oxide metabolites become to have unstable bonds and convert to nitrogens to yield very rapid disappearance of nitric oxide metabolites.

FIG. 6 shows the test result report of chemical measurement of the amount of fixated nitric oxide metabolites. As a test material, a fermented substance using garlic, cabbage, onion, bean sprouts, lettuce, soybean, or cricket, and sodium nitrite were used. The nitrite concentration at fermentation end point was found to be as follows: garlic; 265 mg/L, cabbage; 170 mg/L, onion; 205 mg/L, bean sprouts; 160 mg/L, lettuce; 280 mg/L, soybean; 210 mg/L, and cricket; 179 mg/L. The release amount of nitric oxide from each test sample at acidic condition like artificial stomach was measured and the results are as follows: garlic; 227.7 mg/L, cabbage; 64.8 mg/L, onion; 195 mg/L, bean sprouts; 155.1 mg/L, lettuce; 261 mg/L, soybean; 204.6 mg/L, cricket; 62.5 mg/L, and sodium nitrite; 130.7 mg/L. Moreover, the release amount of nitric oxide at reducing condition mimicking the intestinal condition of human body was measured and the results are as follows: garlic; 702.9 mg/L, cabbage; 162 mg/L, onion; 287 mg/L, bean sprouts; 351 mg/L, lettuce; 450 mg/L, soybean; 411 mg/L, cricket 156.2 mg/L, and sodium nitrite; 488.4 mg/L. Finally, samples after measurement at acidic or reduction condition were collected and the concentration of nitrite ion in the samples was measured. As a result, from all samples other than sodium nitrite (residual nitrite ion concentration of 5 mg/L), nitrite ion was not detected. This result suggests that, when the fermented substance of the present invention is consumed, almost complete conversion from nitric oxide metabolites to nitric oxide is obtained so that there is no risk of having cancer as almost no nitrite ions remain.

Example 2. Comparison of Nitric Oxide Productivity Between Optimized Method for Fixating and Stabilizing Nitric Oxide Metabolites and Conventional Method The inventors of the present invention compared the nitric oxide productivity between a conventional method for fermentation of a nitrogen-containing natural substance (i.e., Korean Patent Application Publication No. 2015-0121970) and the optimized method for fixating and stabilizing nitric oxide metabolites of the present invention.

As the result is illustrated in FIG. 7, compared to the conventional method (i.e., before process optimization), the productivity of nitric oxide metabolites is higher after fermentation for 11 days, i.e., at least 1.9 times (bean sprouts) to 3.0 times or more (garlic), according to the method for fixating and stabilizing nitric oxide metabolites based on fermentation of nitrogen-containing natural substance as described in the present invention (i.e., after process optimization). The conventional fermentation process includes the first fermentation step and the second fermentation step and has only a small production amount of nitric oxide metabolites. On the other hand, the method of the present invention is advantageous in that, as it adopts a batch fermentation process in which both process steps are combined into a single step, the process improvement is achieved and fermentation condition is optimized to maximize the fermentation efficiency, thus yielding higher productivity of nitric oxide metabolites and requiring shorter fermentation time.

Example 3. Comparison of Nitric Oxide Metabolite Productivity Among Different Fermentative Strains At the fermentation condition with temperature, concentration of dissolved oxygen, and chemical oxygen demand at end point which have been optimized in Example 1 above, nitric oxide metabolite productivity was compared and analyzed by using microorganisms other than *Bacillus subtilis*. The fermentative strains used for the test include *B. amyloliquefaciens, B. natto, Lactobacillus bulgaricus*, and *L. rhamnosus*. For the test, the fermented substance obtained after fermentation for 13 days (*B. natto*) or 12 days (fermentative strains other than *B. natto*) was used for measuring the productivity of nitric oxide metabolites.

Figure 8:
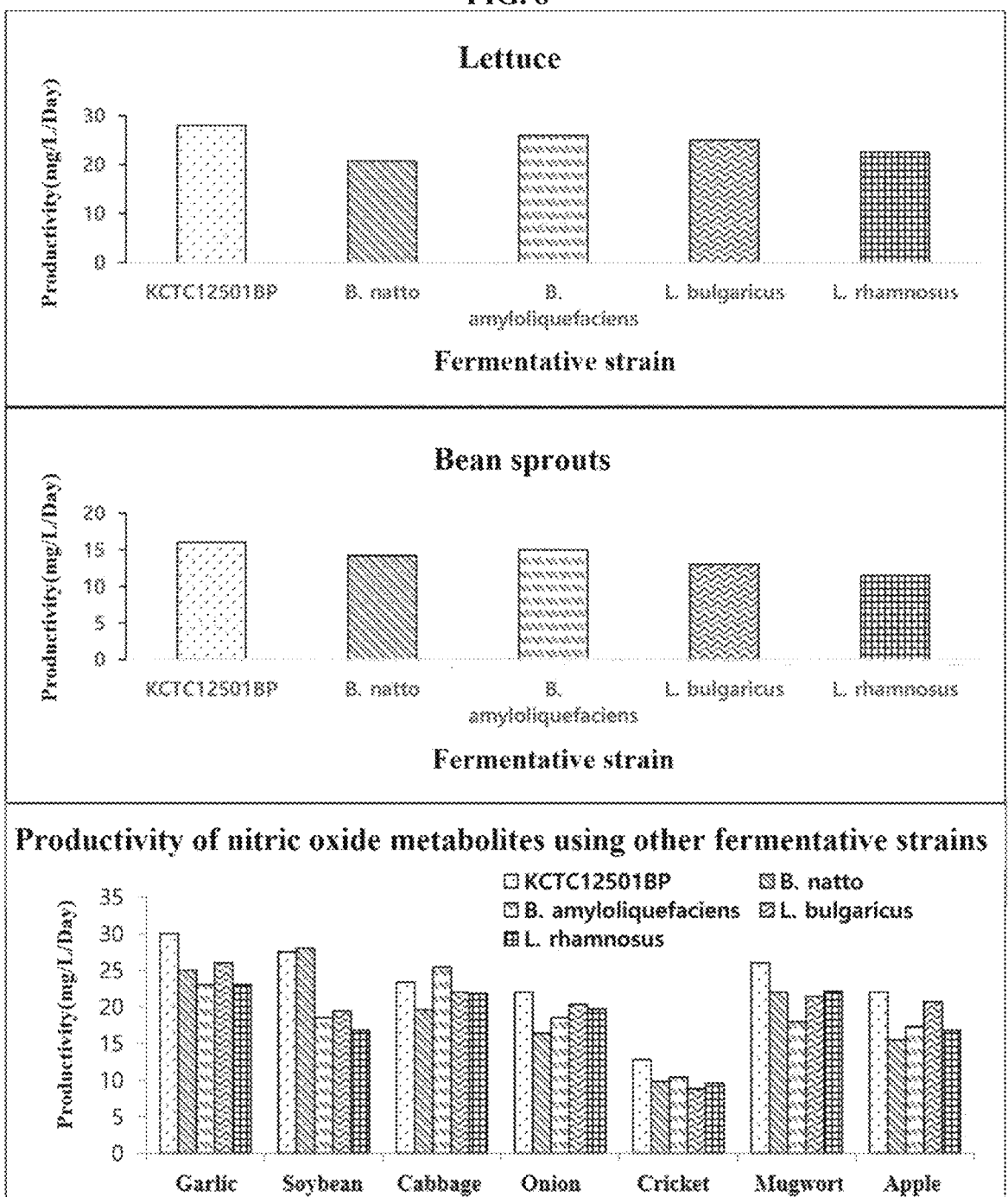
FIG. 8 is a graph showing the productivity of nitric oxide metabolites resulting from different fermentative strains according to the method of the present invention for fixating and stabilizing nitric oxide metabolites based on fermentation of nitrogen-containing natural substance.

As the results are given in FIG. 8 and Table 1, the highest productivity of nitric oxide metabolites was obtained when *Bacillus subtilis*—Chun Hyun Su (Accession Number KCTC12501BP) is used, and also favorable nitric oxide metabolite productivity of from 9 mg/L/day to 28 mg/L/day was obtained with the conditions in which strains other than *Bacillus subtilis*—Chun Hyun Su are used.

TABLE 1

| | Productivity of nitric oxide metabolites among various fermentative strains | | |
| --- | --- | --- | --- |
| Name of strain | Raw material | Nitric oxide metabolites (mg/L) | Productivity (mg/L/Day) |
| *Bifidobacterium bifidum* | Lettuce | 180 | 16.0 |
| *Bifidobacterium longum* | Lettuce | 158 | 17.8 |
| *Bifidobacterium infantis* | Onion | 160 | 20.4 |
| *Enterococcus faecium* | Lettuce | 160 | 20.0 |

TABLE 1-continued

| | Productivity of nitric oxide metabolites among various fermentative strains | | |
| --- | --- | --- | --- |
| Name of strain | Raw material | Nitric oxide metabolites (mg/L) | Productivity (mg/L/Day) |
| *Enterococcus faecalis* | Soybean | 228 | 16.2 |
| *Lactobacillus helveticus* | Cabbage | 132 | 13.7 |
| *Lactobacillus gasseri* | Peanut | 147 | 22.1 |
| *Lactococcus lactis* | Spinach | 165 | 20.9 |
| *Weissella cibaria* | Lettuce | 172 | 18.3 |

Example 4. Determination of Stability of Nitric Oxide Metabolites that are Fixated in Fermented Natural Substance The inventors of the present invention stored the fermented substances, which have been prepared at temperature and concentration of dissolved oxygen conditions, and different concentration ranges of chemical oxygen demand at end point as optimized in Example 1, at room temperature, and, 3 months, 6 months, 1 year, 2 years, and 3 years after the storage, measured and analyzed the content of nitric oxide metabolites in each fermented substance.

Figure 9:
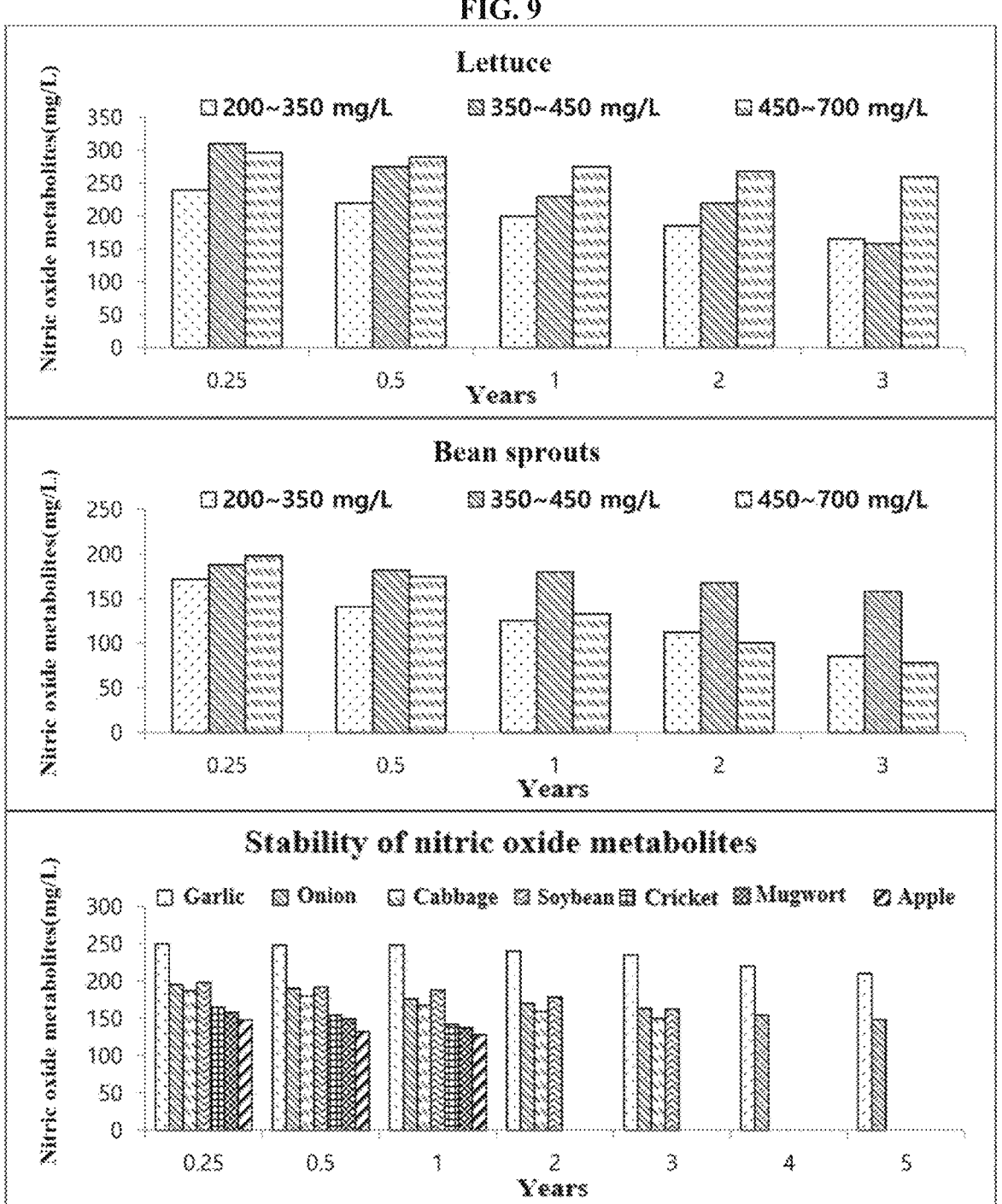
FIG. 9 is a graph showing the stability of the nitric oxide metabolites fixated in fermented substance of the nitrogen-containing natural substance, which has been produced according to the method of the present invention.

As the result is illustrated in FIG. 9, it was observed that content of nitric oxide metabolites in fermented substance somewhat decreases as the storage period is extended. However, for each nitrogen-containing natural substance, the decreasing tendency of content of nitric oxide metabolites is minor in the optimized chemical oxygen demand range at fermentation end point. Specifically, in case of the fermented lettuce, 12% content decrease of nitric oxide metabolites (i.e., 296.3 mg/L→260 mg/L) was observed from 450 to 700 mg/L, which is the optimum chemical oxygen demand range. In case of the fermented bean sprouts, 16% content decrease of nitric oxide metabolites (i.e., 188 mg/L→158 mg/L) was observed from 350 to 450 mg/L, which is the optimum chemical oxygen demand range. Based on those results, it was found that the fermented nitrogen-containing natural substance which has been fermented at a condition with optimized fermentation temperature, concentration of dissolved oxygen, and chemical oxygen demand at end point has nitric oxide metabolites that are fixated and stabilized in fermented substance.

Example 5. Anti-High Blood Pressure Effect of Fermented Natural Substance Containing Nitric Oxide Metabolites Fermented natural substances used for the test were fermented garlic, fermented soybean, and fermented whey, and they were used after being prepared to have $NO_2^-$ of 235 ppm.

As a test animal, 7-week-old male Sprague Dawley (SD) rat was obtained from Samtako (South Korea) and used. The test animals were acclimated to lab environment (temperature: $23\pm1°$ C., humidity: 55% to 60%, photoperiod: 12 hours of light and 12 hours of darkness) for 1 week while they have free access to basic feeds and water.

The acclimated SD rat (8-week-old) was intraperitoneally injected with DOCA (deoxycorticosterone acetate; TCI, Japan) at concentration of 25 mg/kg, twice per week for 4 weeks, and induced to have high blood pressure by using 1% aqueous solution of sodium chloride as drinking water. To determine an occurrence of high blood pressure, blood pressure was measured by using tail-cuff plethysmography (Muromachi Kikai, Japan), and animals with systolic blood pressure of at least 140 mmHg were selected and used for the test.

The test animals were divided into the following 7 groups; control group administered with distilled water, in which an animal model of blood pressure previously had intraperitoneal injection of DOCA and diet of regular feeds and 1% sodium chloride solution (HTC, n=5), group orally administered with garlic fermentation extract (GFO, n=5), group enterally administered with garlic fermentation extract (GFG, n=5), group orally administered with soybean fermentation extract (BFO, n=5), group enterally administered with soybean fermentation extract (BFG, n=5), group orally administered with whey fermentation extract (WFO, n=5), and group enterally administered with garlic fermentation extract (WFG, n=5).

Figure 10:
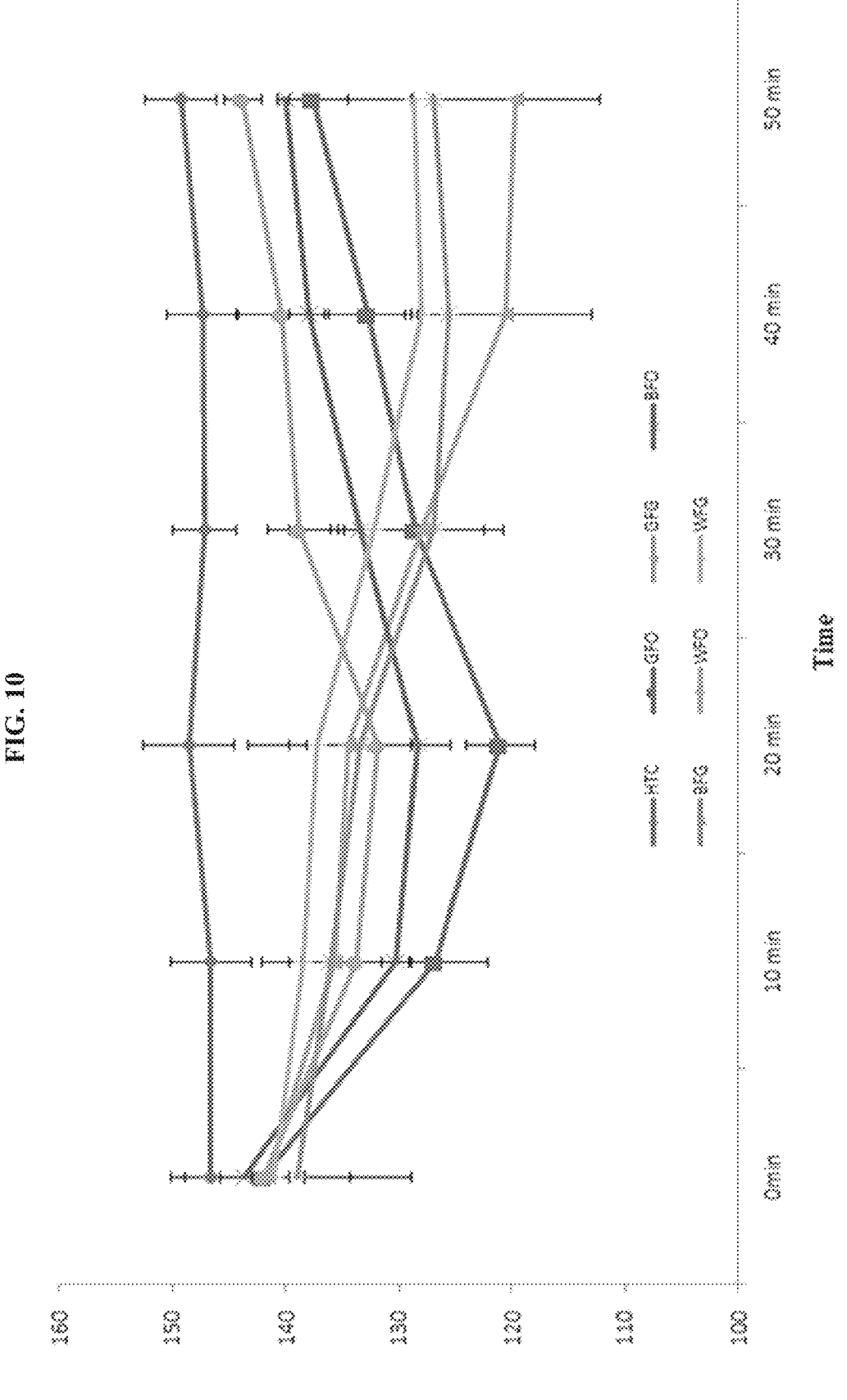
FIG. 10 is the result of determining anti-high blood pressure effect of the fermented natural substance containing nitric oxide metabolites, in which HTC: control group administered with distilled water, in which an animal model of blood pressure previously had intraperitoneal injection of DOCA and diet of regular feeds and 1% sodium chloride solution, GFO: group orally administered with garlic fermentation extract, GFG: group enterally administered with garlic fermentation extract, BFO: group orally administered with soybean fermentation extract, BFG: group enterally administered with soybean fermentation extract, WFO: group orally administered with whey fermentation extract, and WFG: group enterally administered with garlic fermentation extract.

As a result of measuring blood pressure after administering each fermentation extract to a rat having DOCA-induced high blood pressure, it was found that, between 10 minutes and 20 minutes after the oral administration of a test sample, a decrease in the blood pressure is shown in order of fermented garlic (GF), fermented soybean (BF), and fermented whey (WF). In case of the direct enteral administration of a test sample, it was found that, between 30 minutes and 40 minutes after the administration of a test sample, a decrease in the blood pressure is shown in order of fermented garlic (GF), fermented soybean (BF), and fermented whey (WF) (FIG. 10). It is noted that oral administration (GFO, BFO, and WFO) exhibits faster initial effect of lowering blood pressure than enteral administration (GFG, BFG, and WFG) but the blood pressure starts to increase again 20 minutes after the oral administration. On the other hand, in case of the enteral administration group, the effect of lowering blood pressure is exhibited slowly for a long period of time.

Example 6. Anti-Diabetes Effect of Fermented Natural Substance Containing Nitric Oxide Metabolites Fermented natural substances used for the test were fermented soybean and fermented whey, and they were used after being prepared to have $NO_2^-$ of 235 ppm.

As a test animal, 4-week-old male C57BL/6 mouse was obtained from Samtako (South Korea) and used. The test animals were acclimated for 1 week under the same breeding chamber condition as Example 5 above. The acclimated C57BL/6 mouse was then intraperitoneally injected once with STZ (streptozotocin; Sigma-Aldrich, USA) solution, which has been prepared at concentration of 120 mg/kg in 0.1 M citrate buffer (pH 4.5), to induce diabetes. Two weeks after administering STZ, the mouse was fasted for 16 hours and blood was taken from tail vein of the test animal to measure fasting blood glucose using a simple blood glucose meter (Glucotrend, Roche, Germany). As a result, test animals with fasting blood glucose of not more than 200 mg/dL were excluded from the test. Body weight, feed intake amount, and blood glucose level were measured twice a week. After one week, blood glucose level was measured again and test animals which maintained fasting blood glucose of not less than 200 mg/dL were selected and used for the test.

The test animals were divided into the following groups; group administered with distilled water (CON), group orally administered with fermented whey (MP-BY [p.o]), group enterally administered with fermented whey (MP-BY [p.i]), group orally administered with fermented soybean (SB

Figure 11:
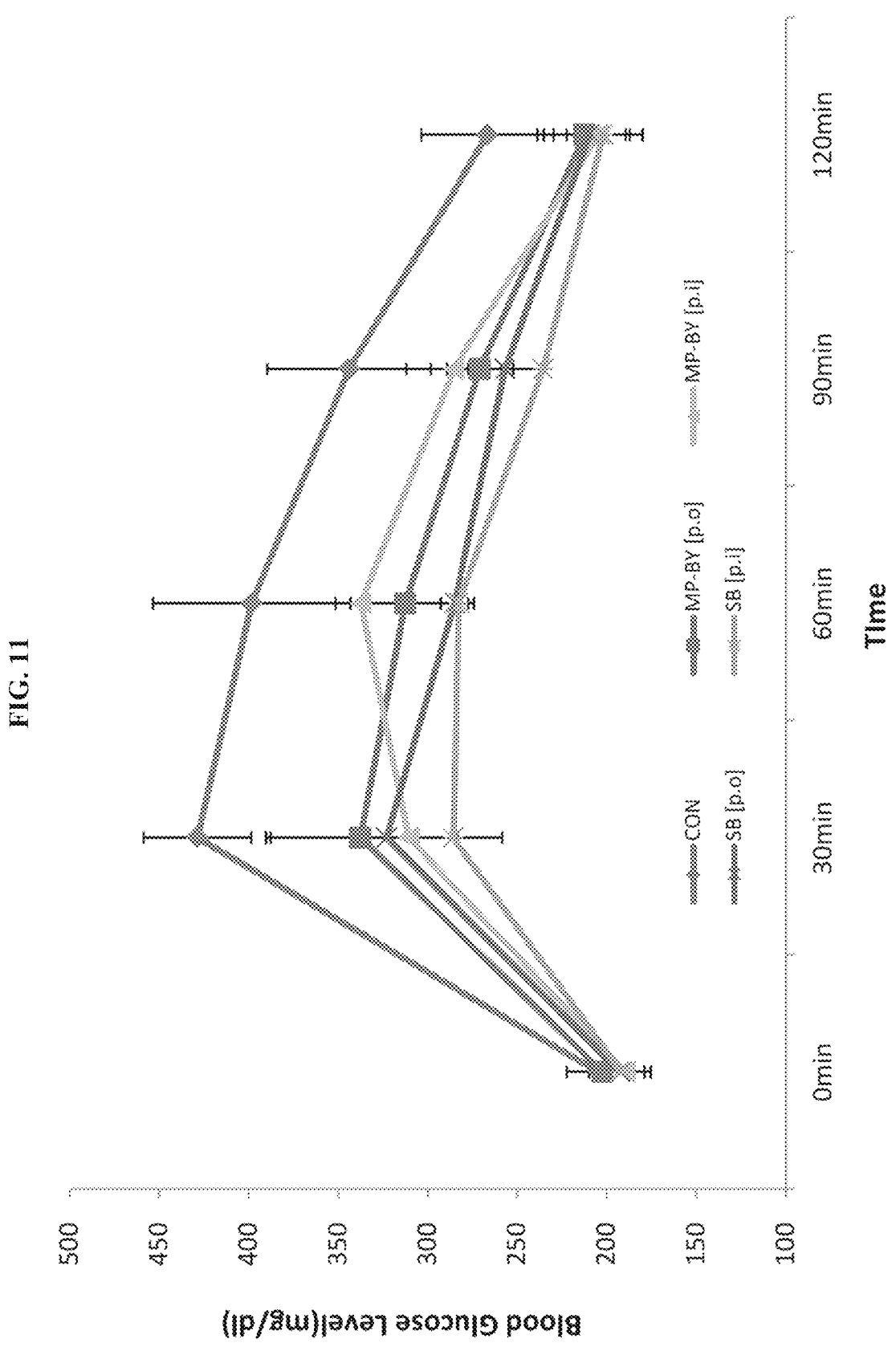
FIG. 11 is the result of determining anti-diabetes effect of the fermented natural substance containing nitric oxide metabolites, in which CON: group administered with distilled water, MP-BY [p.o]: group orally administered with fermented whey, MP-BY [p.i]: group enterally administered with fermented whey, SB [p.o]: group orally administered with fermented soybean, and SB [p.i]: group enterally administered with fermented soybean.

[p.o]), and group enterally administered with fermented soybean (SB [p.i]). After fasting for 12 hours or longer before the test, fasting blood glucose level was measured by drawing blood from tail vein and it was set at initial blood glucose level. Then, the test sample was administered for each test group. Thirty minutes after the administration, the test animal was orally administered with glucose in an amount of 2 g/kg. After that, blood glucose level was determined from tail vein with an interval of 30 minutes, 60 minutes, 90 minutes, or 120 minutes after the administration. As the result is shown in FIG. 11, it was found that the fermented natural substance of the present invention has higher effect of lowering blood glucose level compared to the control group.

Example 7. Anti-Atopic Effect of Fermented Natural Substance Containing Nitric Oxide Metabolites As a test animal, 5-week old male Balb/c mouse was obtained from Samtako (South Korea) and, after acclimatization for 1 week, used for the test. The breeding chamber for test animal has controlled light and darkness cycle with an interval of 12 hours, and temperature was maintained at 23±2° C. and humidity was maintained at 50 to 60%.

Cabbage fermentation extract was used as a test sample of the test, and, specifically, fermented cabbage which has been prepared according to the method of the present invention was frozen at −80° C. and freeze-dried for 5 days (PVTFD10R, Ilshin Lab, Korea). Thus-obtained powder was dissolved in distilled water and used as a test sample.

The test animals were divided into 6 groups as follows: group not treated with any treatment, which was set as normal group (CON), group administered with distilled water after DNFB (1-fluoro-2,4-dinitrobenzene) coating on right ear (DNFB+DW), group administered with 1 mM nitrite after DNFB coating on right ear (DNFB-N), group administered with 1 mM nitrite and 1 mM citrate after DNFB coating on right ear (DNFB+NCA), group administered with 1 mM citrate after DNFB coating on right ear (DNFB+CA), group administered with 1 mM citrate and test sample after DNFB coating on right ear (DNFB+NP), and group administered with test sample after DNFB coating on right ear (DNFB+P). With regard to the selection of the number of animals constituting each group, the minimum number allowing the representation of statistical significance was employed based on 3R principle.

After acclimatization for 1 week, hair in the back area of Balb/c mouse was shaven and the animal was acclimated for 3 days. DNFB reagent was diluted in acetone:olive oil (4:1) to give 0.5% DNFB. On day 3 after the shaving, 0.5% DNFB (50 μl) was applied on the back area to induce skin sensitization. On day 5 after the skin sensitization, each test group except normal group received coating of 0.3% DNFB (challenge), i.e., 20 μl on right ear, to induce atopic dermatitis. The test sample was then applied for 12 days to each group. Each of normal group (CON) and control group (DNFB) was applied with DW, while other groups were applied with each test sample, twice a day. The animal test was carried out by following Guide for Animal Experimentation (GAE).

Anti-atopic effect was analyzed based on visual examination, ear swelling, measurement of interferon γ in blood serum, and histopathological examination.

Visual examination is a clinical evaluation method which is generally employed for atopic dermatitis. To measure the severity of symptoms of atopic dermatitis, evaluation was made for each of the following five items and evaluation scores were added to have a total. The evaluation items are erythema, pruritus and dry skin, edema and excoriation, erosion, and lichenification. For each item, evaluation was made as follows: no symptom (score 0), weak symptom (score 1), mild symptom (score 2), and strong symptom (score 3), and, after adding each result, score of from 0 to 15 was given. As a result of the visual examination, control group treated only with DNFB showed atopic skin changes such as erythema, dry skin, erosion, edema, and excoriation compared to the left ear which has not received any treatment. As a result of comparing the observation results, which have been collectively obtained from various symptoms of atopic dermatitis, it was found that, in terms of score, visual examination score is lower in a significant sense in all groups applied with test sample except control group (DNFB+DW) (A of FIG. 12).

Measurement of ear thickness was performed by following a change in the thickness for 5 days by using vernier calipers (Mitutoyo Co., Kanagawa, Japan). As a result, the change in ear thickness on day 2 after test sample application shows an increase by 182.4±15.9% in control group (DNFB+DW) while an increase by 66.7±19.9% or 100.0±17.7% is shown from the groups administered with a test sample (i.e., DNFB+NP and DNFB+P), indicating a less increase in a significant sense compared to control group (B of FIG. 12).

With regard to cytokine in blood serum, production amount of interferon γ was measured by using ELISA kit (R&D Systems, Minneapolis, USA). As a result of the measurement, the groups administered with a test sample (i.e., DNFB+NP and DNFB+P) showed the amount of 17.93±0.06 pg/mL and 20.77±0.08 pg/mL, respectively, representing a lower interferon γ value compared to control group (DNFB, 27.33±0.84 pg/mL), and the decrease in a significant sense was shown from all groups administered with a test sample (C of FIG. 12).

Histopathological test was carried out as follows. Ear tissues were removed on the last day of test, cleaned with physiological saline, and dried using a filter paper. Part of the liver tissues removed for the histopathological test was fixated in neutral 10% formalin, subjected to paraffin embedding using a common method for histopathological test, and cut to a thickness of 4 μm to prepare a slide. Thus-prepared slide was stained with Hematoxylin & Eosin (H&E), and then observed under optical microscope Olympus DP70 (Olympus Optical Co., Japan). As a result, it was shown that there is a decrease in ear thickness in a significant sense in the groups administered with a test sample when compared to DNFB group as a control (Table 2).

TABLE 2

| Analysis of ear thickness of mouse with DNFB-induced atopic dermatitis | |
| --- | --- |
| Group | Ear thickness (μm) |
| DNFB + DW | 843.17 ± 55.22 |
| DNFB + N | 463.67 ± 77.08 |
| DNFB + NCA | 441.00 ± 55.90 |
| DNFB + CA | 593.17 ± 71.27 |
| DNFB + NP | 452.23 ± 76.48 |
| DNFB + P | 555.33 ± 71.04 |

Example 8. Skin Cell Regeneration Effect of Fermented Natural Substance Containing Nitric Oxide Metabolites The test animal and test sample (cabbage fermentation extract) used in Example 8 are the same as those described in Example 7 above. One week after the acclimatization, hair on the back of the test animal was shaven under inhaled anesthesia using isoflurane. Thereafter, by using a punch used for leather (4 mm, Kai Medical, China), a circular and bilaterally symmetric skin damage was created at two spots to induce a wound. The test animals were divided into 6 groups as follows: control group in which distilled water was applied to the wound area after inducing wound (WHD), group treated with 1 mM nitrite coating solution on wound area (WHN), group treated with 1 mM nitrite and 1 mM citrate coating solution on wound area (WHNCA), group treated with 1 mM citrate coating solution on wound area (WHCA), group treated with 1 mM citrate and test sample coating solution on wound area (WHNP), and group treated with sample coating solution on wound area (WHP).

Figure 13:
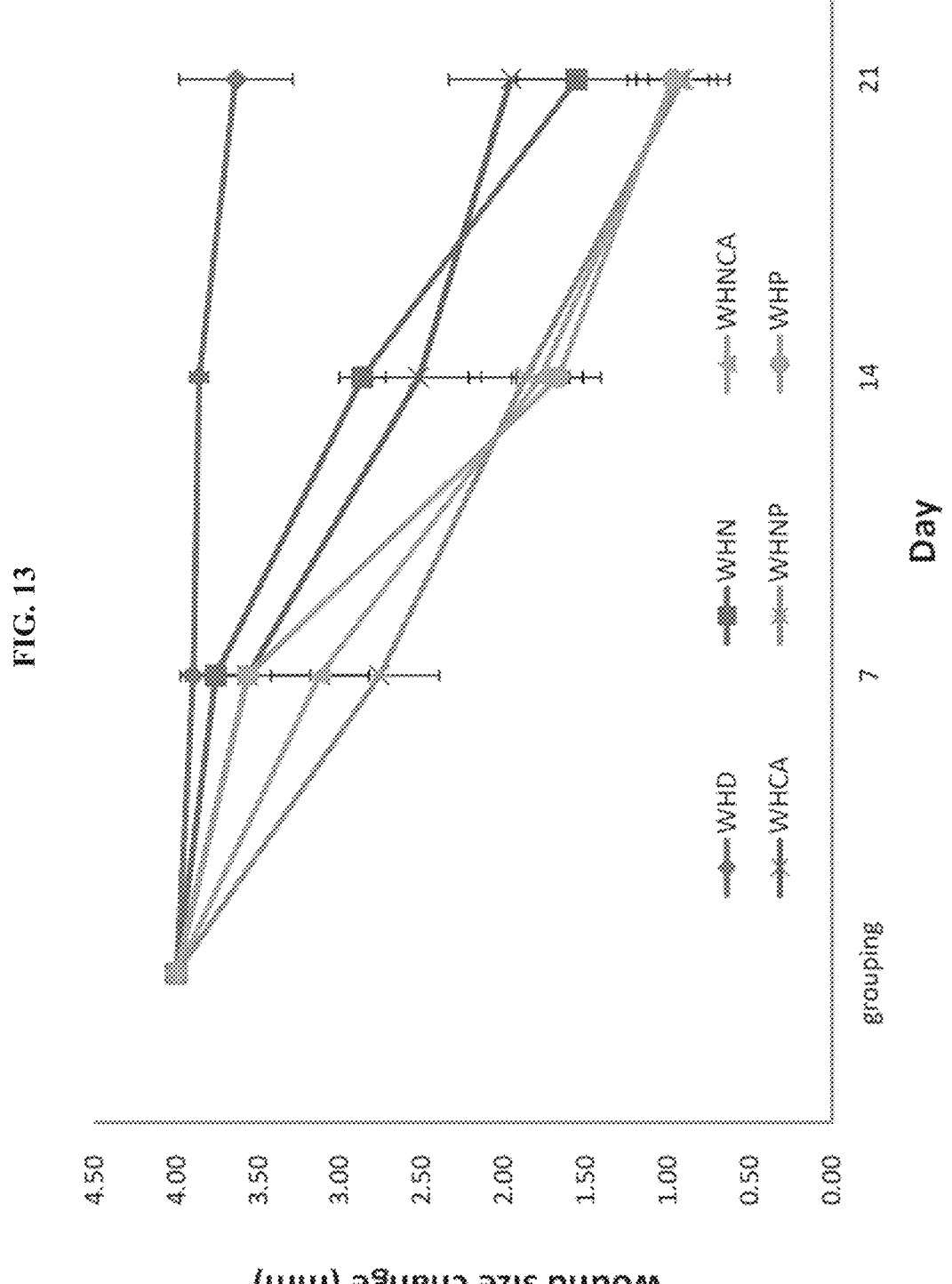
FIG. 13 shows the result of determining, for each test group, a change in wound area after inducing a wound, in which WHD: control group in which distilled water was applied to the wound area after inducing wound, WHN: group treated with 1 mM nitrite coating solution on wound area, WHNCA: group treated with 1 mM nitrite and 1 mM citrate coating solution on wound area, WHCA: group treated with 1 mM citrate coating solution on wound area, WHNP: group treated with 1 mM citrate and test sample coating solution on wound area, and WHP: group treated with sample coating solution on wound area.
Figure 14:
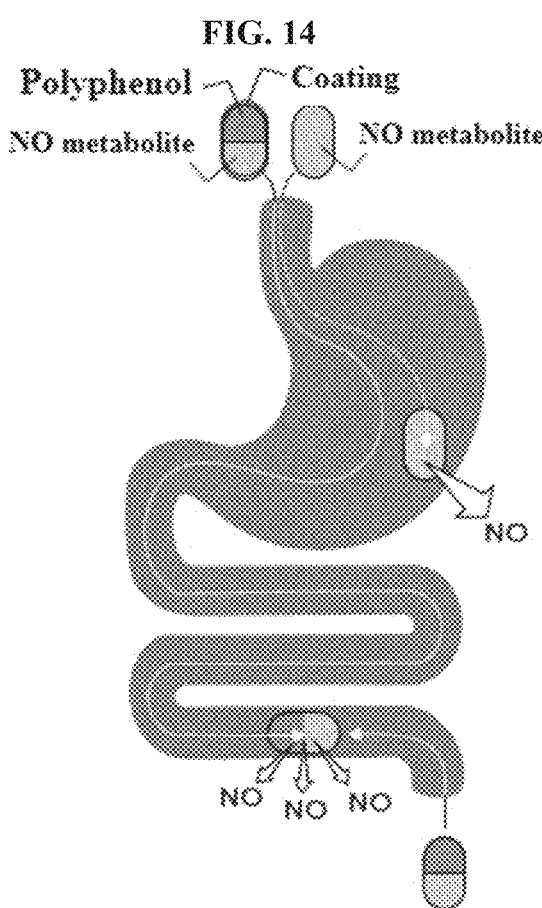
FIG. 14 is a drawing in which nitric oxide production by a fermentation material having mixture of nitric oxide metabolites and polyphenol is compared between the enteral production and the intragastric production of nitric oxide.

Until day 21 after inducing wound, a change in area of wound was examined for individual animals which have been randomly selected from the group with induced wound. As a result, it was found that the amount of effusion is high in wound area with inflammation and foreign materials like grass bedding stuck on the wound area. Two weeks after inducing wound, scab started to form on the inflammation area. Three weeks and thereafter, a difference in skin regeneration area was shown depending on the type of a test sample. Compared to control group, all groups applied with a test sample showed wound area reduced in a significant sense (FIG. 13).

Example 9. Anti-High Blood Pressure and Anti-Diabetes Effect of Enteric-Coated Tablet which Comprises Fermented Natural Substance Containing Nitric Oxide Metabolites and Polyphenol When various plants rich in polyphenol are used, it is possible to obtain fermentation liquid containing both nitric oxide metabolites and polyphenol. In this example, fermented liquid obtained by fermenting Korean garlic was used for the test after concentration. Content of the nitric oxide metabolites in garlic fermentation concentrate which has been obtained after concentration was adjusted such that it is 200 ppm or higher in terms of $NO_2^-$. It is preferable that the concentration step is carried out for 24 hours to 48 hours at temperature of 20° C. to 30° C. and stirring speed of 100 rpm to 300 rpm.

9-1. Measurement of Content of Nitric Oxide Metabolites

By adding zinc powder (zinc powder in solid state does not cause any volume change of the liquid, thus yielding no decrease in the concentration), all $NO_2^-$ and $NO_3^-$ contained in concentrate were reduced to $NO_2^-$ and total concentration of $NO_2^-$ was measured. Accordingly, total content of the nitric oxide metabolites was determined.

More specifically described, to measure the total concentration of $NO_2^-$, zinc powder was added first and the concentrate was reduced for 1 hour. Then, the resulting concentrate was diluted by 1000 times with distilled water and centrifuged at 3000 rpm to separate insoluble polyphenol and diet fiber. Clear supernatant was collected (50 μl) and used as a measurement sample. Each of the $NO_2^-$ reference solution (50 μl) and measurement sample (50 μl) was aliquoted to a 96-well plate, added with a test solution (100 μl, solution obtained by mixing 30% acetic acid containing 1% sulfanilamide with 60% acetic acid containing 0.1% N-(1-naphthyl)ethylenediamine at ratio of 1:2), and allowed to stand at room temperature for 10 minutes to induce a chromogenic reaction. Subsequently, absorbance value was measured for each well at wavelength of 570 nm using multi-plate reader. By comparing the absorbance value between the reference solution and test sample, $NO_2^-$ concentration was calculated.

For preparing an enteric-coated tablet, the fermented liquid containing nitric oxide metabolites was concentrated, freeze-dried, or dried by hot air to give powder, which was then subjected to enteric-coated tablet coating. Alternatively, an enteric-coated tablet was prepared by using a product which has been obtained by adding powder containing nitric oxide metabolites and polyphenols e.g., anthocyanins beneficial for eye health, resveratrol beneficial for heart function, catechin beneficial for brain and obesity control, silymarin beneficial for liver health, polyphenol having activity on other health functions, and the like, or by mixing and fermenting them to enhance the efficacy of each component.

9-2. Blood Pressure-Lowering Effect in Test Animal of High Blood Pressure

Test animals of high blood pressure prepared in Example 5 were subjected to the treatment by following the processes described below, and then blood pressure was measured for all test animals with an interval of 15 minutes, 30 minutes, 60 minutes, and 120 minutes; control group: rat injected with DOCA without being administered with a test sample (i.e., garlic fermentation concentrate obtained by concentration), comparative group; rat injected with DOCA after oral administration of $NaNO_2$ (18.6 mg/kg, (in terms of the amount of $NO_2^-$, 12.5 mg/kg)) once a day for 4 weeks, and treatment group; rat injected with DOCA after rectal administration of a test sample (in terms of the total amount of $NO_2^-$, 12.5 mg/kg) once a day for 4 weeks.

Figures 15, 16:
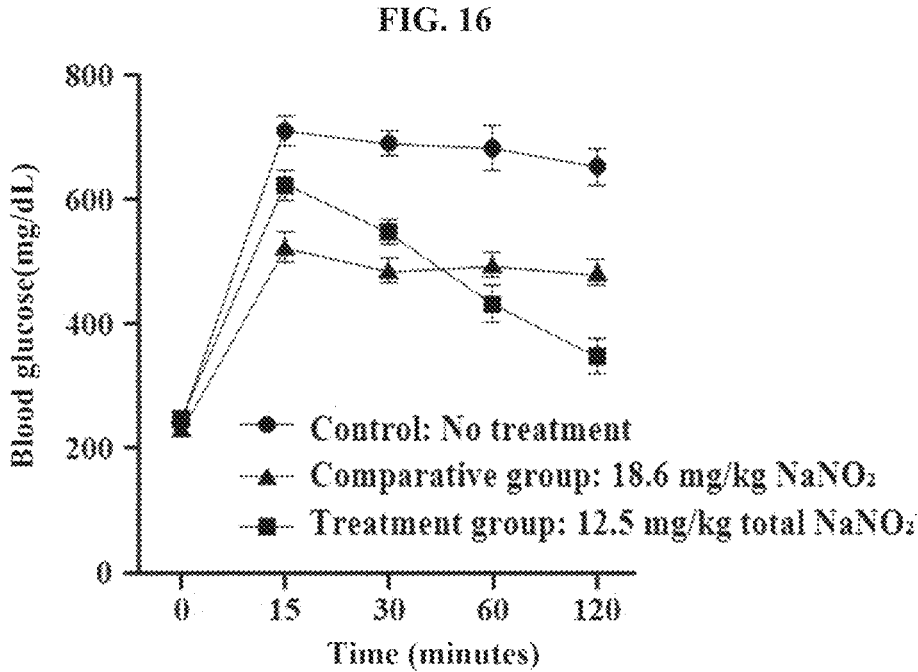
FIG. 15 shows the result of determining, in a test model of high blood pressure, the effect of rectal administration of a mixture of nitric oxide metabolites/polyphenol and oral administration of $NaNO_2$ on blood pressure, in which the determination was made with a certain time interval.
FIG. 16 shows the result of determining, in a test model of diabetes, the effect of rectal administration of a mixture of nitric oxide metabolites/polyphenol and oral administration of $NaNO_2$ on blood glucose level, in which the determination was made with a certain time interval.

As the result is illustrated in FIG. 15, when the rat of control group induced to have high blood pressure (circles in FIG. 15) was administered with distilled water and a change in blood pressure was monitored over time, it was observed that there is no significant change in the blood pressure. However, in case of comparative group (i.e., DOCA injection after oral administration of $NaNO_2$), it is acknowledged that a rapid decrease in blood pressure was caused as $NaNO_2$ is quickly reduced to nitric oxide by catalytic gastric juice in stomach and absorbed in human body (triangles in FIG. 15). In case of the treatment group, it is understood that, due to the polyphenol catalyst contained in test sample, the nitric oxide metabolites in fermented substance are reduced to nitric oxide and absorbed in human body at relatively slow rate, yielding gradual decrease in the blood pressure (squares in FIG. 15). Based on those results, it was possible to acknowledge the fact that the test sample used for measuring blood pressure change in the present invention can generate, even in intestinal environment, nitric oxide at a concentration that is effective for lowering blood pressure.

In particular, according to another aspect of the test result of blood pressure measurement in FIG. 15, it was observed from comparative group which has been orally administered with $NaNO_2$ that, after the sharp decrease in initial blood pressure, the blood pressure has dramatically increased again. On the other hand, in case of the treatment group which received rectal administration of test sample, the blood pressure has continuously and gradually decreased. Those observation results are believed to be caused by the test sample used for measurement of the present invention, which produce nitric oxide in intestinal environment over a certain period of time.

9-3. Oral Glucose Tolerance Test for Test Animal of Diabetes

Oral glucose tolerance test (hereinbelow, abbreviated as "OGTT") was carried out for the test animals of diabetes prepared in Example 6 above, in which the test was carried out according to the following processes, and the results are shown in FIG. 16 in which control group: mouse injected with STZ after being administered with distilled water, comparative group; mouse injected with STZ after oral administration of $NaNO_2$ (18.6 mg/kg (in terms of the amount of $NO_2^-$, 12.5 mg/kg)) once a day for 4 weeks, and treatment group; mouse injected with STZ after rectal administration of a test sample (fermented garlic concentrate, 12.5 mg/kg) once a day for 4 weeks. Subsequently, all test animals were orally administered with glucose (2 g/kg), and then blood glucose level was measured with an interval of 15 minutes, 30 minutes, 60 minutes, and 120 minutes to complete the OGTT.

According to one aspect of the result of OGTT of FIG. 16, when control group with diabetes was administered with glucose, blood glucose level has increased quickly and stayed at that level without showing any decrease (circles in FIG. 16). On the other hand, in case of comparative group, it is understood that a rapid decrease in blood glucose level was caused as $NaNO_2$ is quickly reduced to nitric oxide by catalytic gastric juice in stomach and absorbed in human body (triangles in FIG. 16). In case of the treatment group, it is understood that, due to the polyphenol as a catalyst contained in test sample, the nitric oxide metabolites in fermented substance are reduced to nitric oxide and absorbed in human body at relatively slow rate, yielding gradual decrease in blood glucose level (squares in FIG. 16). Based on those results, it was possible to acknowledge the fact that the test sample used for measurement of the present invention can generate, even in intestinal environment, nitric oxide at a concentration that is effective for lowering blood glucose level.

In particular, according to another aspect of the OGTT result in FIG. 16, it was observed that, after showing a decrease in initial blood glucose, no further decrease in the blood glucose level was observed in comparative group which has been orally administered with $NaNO_2$. On the other hand, in case of the treatment group which received rectal administration of test sample, the blood glucose level has continuously decreased. Those observation results are believed to be caused by the test sample used for measurement of the present invention, which produce nitric oxide in intestinal environment over a certain period of time.

9-4. Anti-Diabetes Effect and Effect of Alleviating Symptoms of Diabetes Complications in Test Animal of Diabetes To the test animal of diabetes prepared in Example 6, $NaNO_2$ was administered orally once a day for 4 weeks or the test sample (garlic fermentation concentrate obtained by concentration) was administered rectally also once a day for 4 weeks. On the last day of test, blood was collected from all test animals to complete the test. After that, content of blood glucose, glycated hemoglobin, insulin, creatinine, and urea nitrogen in the collected blood were measured by using a diagnostic kit. The results are shown in Table 3. Specifically, the blood glucose, glycated hemoglobin, and insulin of Table 3 were used for determining and analyzing the anti-diabetes effect, while creatinine and urea nitrogen of Table 3 were used for determining and analyzing the effect of alleviating the symptoms of diabetes complications. A decrease in kidney function is one of the diabetes complications, and creatinine and urea nitrogen are a clinical biomarker for measuring the kidney function.

TABLE 3

| | Normal group (normal) | Control group | Comparative group | Treatment group |
|---|---|---|---|---|
| Content of blood glucose, glycated hemoglobin, insulin, creatinine, and urea nitrogen in each test group | | | | |
| Fasting blood glucose (mg/dL) | 106.0 ± 5.0 | 480.0 ± 6.0 | 320.0 ± 11.0 | 250.0 ± 3.0 |
| Glycated hemoglobin (%) | 3.7 ± 0.4 | 7.5 ± 0.3 | 6.2 ± 0.3 | 5.1 ± 0.2 |
| Insulin (ng/mL) | 380.6 ± 23.1 | 80.0 ± 10.7 | 150.0 ± 9.5 | 200.0 ± 5.3 |
| Creatinine (mg/dL) | 0.12 ± 0.03 | 0.25 ± 0.05 | 0.18 ± 0.03 | 0.15 ± 0.02 |
| Urea nitrogen (mg/dL) | 20.2 ± 2.3 | 43.2 ± 0.8 | 37.1 ± 0.5 | 30.0 ± 0.7 |

When fasting blood glucose level is compared between normal group and control group in Table 3 above, it was observed that control group with induced diabetes has high blood glucose level while comparative group orally administered with $NaNO_2$ for 4 weeks and the treatment group rectally administered with a test sample for 4 weeks have relatively low blood glucose level, supporting that the nitric oxide metabolites indeed have an anti-diabetes effect. Meanwhile, in terms of the anti-diabetes effect, it was observed that the treatment group is better than comparative group. In terms of a change in glycated hemoglobin and insulin, it was also observed that more excellent anti-diabetes effect is obtained from the treatment group rectally administered with a test sample for 4 weeks than comparative group orally administered with $NaNO_2$ for 4 weeks, showing a good match with the above result. Moreover, when blood creatinine and urea nitrogen as an indicator of kidney function are compared between normal group and control group in Table 3 above, it was observed that control group with induced diabetes has higher values, and it is understood to be one of diabetes complications caused by a decrease in kidney function resulting from aggravated diabetes. Since the impaired kidney function observed from control group is improved in comparative group orally administered with $NaNO_2$ for 4 weeks and also the treatment group rectally administered with a test sample for 4 weeks when compared to control group, it was found that the nitric oxide metabolites indeed have an effect of alleviating the symptoms of diabetes complications. Meanwhile, it was observed that the treatment group has more excellent effect than comparative group in terms of the effect of alleviating the symptoms of diabetes complications.

*Bacillus subtilis*—Chun Hyun Su strain was deposited in the Korea Research Institute of Bioscience and Biotechnology (having the address of 181, Ipsin-gil, Jeongeup-si, Jeolllabuk-do 56212, Republic of Korea) under the Access number of KCTC 12501BP on Oct. 7, 2013. The deposit has been made under the terms of the Budapest Treaty and all restrictions imposed by the depositor on the availability to the public of the biological material will be irrevocably removed upon the granting of a patent.

What is claimed is:

1. A method of fixating and stabilizing nitric oxide metabolites within fermented natural substance, the method comprising:

adding a fermentative strain to nitrogen-containing natural substance and carrying out fermentation by a batch fermentation process, wherein the nitrogen-containing natural substance is at least one selected from the group consisting of lettuce, *Sedum sarmentosum*, spinach, blueberry, dandelion, pomegranate, cabbage, garlic, *Morinda citrifolia*, onion, soybean, bean sprout, mulberry leaf, *Momordica charantia, Rubus coreanus, Houttuynia cortada*, aronia, *Humulus japonicus*, *Coptis chinensis*, hijiki, hooker chive, mushrooms, calamus, wild spinach (Seomcho), Chinese cabbage, kelp, apple, mugwort, orange, salmon testis, abalone shell, shellfish shell, cricket, silkworm, *Rehmannia glutinosa*, and Shipjeon-daebo-tang, wherein the fermentation is carried out at a temperature in a range of 18 to 30° C. and a dissolved oxygen level in a range of 0.03 to 0.1 mg/L, and a chemical oxygen demand is 200 to 700 mg/L at an fermentation end point; and the fermentative strain is a strain belonging to *Bacillus* sp., *Bifidobacterium* sp., *Enterococcus* sp., or *Lactobacillus* sp.

2. The method of claim 1, wherein the fermentative strain is at least one selected from the group consisting of *Bacillus subtilis, Bacillus amyloliquefaciens, Bacillus natto, B. licheniformis, Bifidobacterium bifidum, Bifidobacterium infantis, B. longum, Enterococcus faecium, E. faecalis, Lactobacillus acidopilus, L. alimentarius, L. bulgaricus, L. casei, L. curvatus, L. delbrukii, L. johnsonii, L. farciminus, L. gasseri, L. helveticus, L. rhamnosus, L. reuteri*, and *L. sakei*.

3. The method of claim 1, wherein the fermentation is carried out at 30° C. and a dissolved oxygen level of 0.04 mg/L, and a chemical oxygen demand is 450 to 700 mg/L at an fermentation end point.

4. The method of claim 1, wherein the nitrogen-containing natural substance is lettuce.

5. The method of claim 1, wherein the nitrogen-containing natural substance is bean sprout; and the fermentation is carried out at the following conditions:

fermentation temperature of 30° C.;

dissolved oxygen level of 0.04 mg/L; and chemical oxygen demand is 350 to 450 mg/L at an fermentation end point.

6. The method of claim 1, wherein the fermentative strain is *Bacillus subtilis* deposited in the Korea Research Institute of Bioscience and Biotechnology under the Access number of KCTC 12501BP.

7. The method of claim 6, wherein the nitrogen-containing natural substance comprises lettuce or bean sprout.

8. The method of claim 7, wherein the fermentation is carried out with lettuce at the temperature of 18-30° C., the dissolved oxygen concentration of 0.03-0.1 mg/L, and the chemical oxygen demand of 450-700 mg/L at the fermentation end point.

9. The method of claim 7, wherein the fermentation is carried out with bean sprout at the temperature of 18-30° C., the dissolved oxygen concentration of 0.03-0.1 mg/L, and the chemical oxygen demand of 350-450 mg/L at the fermentation end point.

10. The method of claim 1, wherein the batch fermentation process is a single batch fermentation process.

11. A method of producing a fermented natural substance having nitric oxide metabolites fixated and stabilized therein, the method comprising:

adding a fermentative strain to nitrogen-containing natural substance and carrying out fermentation by a batch fermentation process, wherein the nitrogen-containing natural substance is at least one selected from the group consisting of lettuce, *Sedum sarmentosum*, spinach, blueberry, dandelion, pomegranate, cabbage, garlic, *Morinda citrifolia*, onion, soybean, bean sprout, mulberry leaf, *Momordica charantia, Rubus coreanus, Houttuynia cortada, aronia, Humulus japonicus, Coptis chinensis*, hijiki, hooker chive, mushrooms, calamus, wild spinach (Seomcho), Chinese cabbage, kelp, apple, mugwort, orange, salmon testis, abalone shell, shellfish shell, cricket, silkworm, *Rehmannia glutinosa*, and Shipjeon-daebo-tang, wherein the fermentation is carried out at a temperature in a range of 18 to 30° C. and a dissolved oxygen level in a range of 0.03 to 0.1 mg/L, and a chemical oxygen demand is 200 to 700 mg/L at an fermentation end point; and the fermentative strain is a strain belonging to *Bacillus* sp., *Bifidobacterium* sp., *Enterococcus* sp., or *Lactobacillus* sp.

12. The method of claim 11, wherein the fermentation is carried out for 2 to 30 days.

\* \* \* \* \*